(12) United States Patent
Robinson et al.

(10) Patent No.: US 10,973,569 B2
(45) Date of Patent: *Apr. 13, 2021

(54) ELECTROSURGICAL TISSUE SEALING DEVICE WITH NON-STICK COATING

(71) Applicant: COVIDIEN LP, Mansfield, MA (US)

(72) Inventors: William E. Robinson, Boulder, CO (US); Michael C. Barden, Corona, CA (US); Kristen P. Bradley, Westminster, CO (US); Todd W. Boucher, Longmont, CO (US)

(73) Assignee: Covidien LP, Mansfield, MA (US)

( * ) Notice: Subject to any disclaimer, the term of this patent is extended or adjusted under 35 U.S.C. 154(b) by 272 days.

This patent is subject to a terminal disclaimer.

(21) Appl. No.: 16/113,808

(22) Filed: Aug. 27, 2018

(65) Prior Publication Data

US 2019/0090935 A1 Mar. 28, 2019

Related U.S. Application Data

(60) Provisional application No. 62/561,812, filed on Sep. 22, 2017.

(51) Int. Cl.
*A61B 18/00* (2006.01)
*A61B 18/14* (2006.01)
(Continued)

(52) U.S. Cl.
CPC ...... *A61B 18/1445* (2013.01); *A61B 18/1206* (2013.01); *A61B 18/1442* (2013.01);
(Continued)

(58) Field of Classification Search
CPC ............ A61B 18/1206; A61B 18/1442; A61B 18/1445; A61B 2018/00083;
(Continued)

(56) References Cited

U.S. PATENT DOCUMENTS 3,729,007 A 4/1973 Mirkovitch
4,100,113 A 7/1978 McCain
(Continued)

FOREIGN PATENT DOCUMENTS

BR P10705283 6/2009
CA 2520413 A1 3/2007
(Continued)

OTHER PUBLICATIONS

Canadian Office Action dated Aug. 29, 2019 issued in corresponding CA Appln. No. 3,015,418.
(Continued)

*Primary Examiner* — Eun Hwa Kim
*Assistant Examiner* — Rachel A. Vierra
(74) *Attorney, Agent, or Firm* — Carter, DeLuca & Farrell LLP

(57) ABSTRACT

An electrosurgical instrument includes a jaw member having an electrically conductive tissue sealing plate configured to operably couple to a source of electrosurgical energy for treating tissue. A polydimethylsiloxane coating having a thickness in the range of from about 35 nm to about 85 nm is disposed on the tissue sealing plate.

6 Claims, 11 Drawing Sheets

(51) Int. Cl.
　　*A61B 18/12*　　(2006.01)
　　*C23C 14/00*　　(2006.01)
　　*B05D 1/00*　　(2006.01)
　　*B05D 3/14*　　(2006.01)

(52) U.S. Cl.
　　CPC .............. *A61B 2018/0013* (2013.01); *A61B 2018/0063* (2013.01); *A61B 2018/00083* (2013.01); *A61B 2018/00136* (2013.01); *A61B 2018/00589* (2013.01); *A61B 2018/00601* (2013.01); *A61B 2018/00791* (2013.01); *A61B 2018/00875* (2013.01); *A61B 2018/126* (2013.01); *A61B 2018/1253* (2013.01); *A61B 2018/1266* (2013.01); *A61B 2018/1412* (2013.01); *A61B 2018/1452* (2013.01); *B05D 1/60* (2013.01); *B05D 1/62* (2013.01); *B05D 3/142* (2013.01); *C23C 14/00* (2013.01)

(58) Field of Classification Search
　　CPC .. A61B 2018/0013; A61B 2018/00136; A61B 2018/00589; A61B 2018/00601; A61B 2018/0063; A61B 2018/00791; A61B 2018/00875; A61B 2018/1253; A61B 2018/126; A61B 2018/1266; A61B 2018/1412; A61B 2018/1452; B05D 1/60; B05D 1/62; B05D 3/142; C23C 14/00
　　See application file for complete search history.

(56) References Cited

U.S. PATENT DOCUMENTS

| | | |
|---|---|---|
| 4,348,426 A | 9/1982 | Blenner et al. |
| 4,396,450 A | 8/1983 | Blenner et al. |
| 4,492,231 A | 1/1985 | Auth |
| 4,714,650 A | 12/1987 | Obayashi et al. |
| 5,201,900 A | 4/1993 | Nardella |
| 5,211,993 A | 5/1993 | Kolesinski |
| 5,213,928 A | 5/1993 | Yu |
| 5,484,436 A | 1/1996 | Eggers et al. |
| 5,549,604 A | 8/1996 | Sutcu et al. |
| 5,702,387 A | 12/1997 | Arts et al. |
| 5,713,895 A | 2/1998 | Lontine et al. |
| 5,773,098 A | 6/1998 | Thomas |
| 5,925,043 A | 7/1999 | Kumar et al. |
| 5,965,629 A | 10/1999 | Jung et al. |
| 6,066,137 A | 5/2000 | Greep |
| 6,070,444 A * | 6/2000 | Lontine ............. A61B 18/1402 72/46 |
| 6,139,547 A | 10/2000 | Lontine et al. |
| 6,146,462 A | 11/2000 | Yializis et al. |
| 6,159,531 A | 12/2000 | Dang et al. |
| 6,293,946 B1 | 9/2001 | Thorne |
| 6,300,641 B1 | 10/2001 | Koh et al. |
| 6,408,755 B1 | 6/2002 | Meisters et al. |
| 6,428,861 B2 | 8/2002 | France et al. |
| 6,486,135 B1 | 11/2002 | Li et al. |
| 6,534,133 B1 | 3/2003 | Kaloyeros et al. |
| 6,548,121 B1 | 4/2003 | Bauer et al. |
| 6,582,429 B2 | 6/2003 | Krishnan et al. |
| 6,602,552 B1 | 8/2003 | Daraskevich et al. |
| 6,730,275 B2 | 5/2004 | Sharma et al. |
| 6,774,018 B2 | 8/2004 | Mikhael et al. |
| 6,869,676 B2 | 3/2005 | Burger et al. |
| 6,932,816 B2 | 8/2005 | Phan |
| 6,951,559 B1 | 10/2005 | Greep |
| 6,953,461 B2 | 10/2005 | McClurken et al. |
| 7,067,405 B2 | 6/2006 | Mikhael et al. |
| 7,083,618 B2 | 8/2006 | Couture et al. |
| 7,147,634 B2 | 12/2006 | Nesbitt |
| 7,156,842 B2 | 1/2007 | Sartor et al. |
| 7,214,413 B2 | 5/2007 | Koulik et al. |
| 7,258,899 B1 | 8/2007 | Sharma et al. |
| 7,288,091 B2 | 10/2007 | Nesbitt |
| 7,300,859 B2 | 11/2007 | Mikhael et al. |
| 7,377,919 B2 | 5/2008 | Heim et al. |
| 7,390,326 B2 | 6/2008 | Nesbitt |
| 7,566,333 B2 | 7/2009 | Van Wyk et al. |
| 7,588,565 B2 | 9/2009 | Marchitto et al. |
| 7,618,684 B2 | 11/2009 | Nesbitt |
| 7,683,293 B2 | 3/2010 | Buzzi et al. |
| 7,753,908 B2 | 7/2010 | Swanson |
| 7,899,552 B2 | 3/2011 | Atanasoska et al. |
| 7,955,637 B2 | 6/2011 | Nesbitt |
| 7,967,839 B2 | 6/2011 | Flock et al. |
| 7,976,544 B2 | 7/2011 | McClurken et al. |
| 8,814,861 B2 | 8/2014 | Nesbitt |
| 8,865,264 B2 | 10/2014 | Haack et al. |
| 2001/0045351 A1 | 11/2001 | Koh et al. |
| 2003/0036753 A1 | 2/2003 | Morgan et al. |
| 2003/0158548 A1 | 8/2003 | Phan et al. |
| 2003/0158549 A1 | 8/2003 | Swanson |
| 2003/0229344 A1* | 12/2003 | Dycus ................ A61B 18/1445 606/51 |
| 2003/0236518 A1 | 12/2003 | Marchitto et al. |
| 2004/0134770 A1 | 7/2004 | Petersen |
| 2004/0210282 A1 | 10/2004 | Flock et al. |
| 2005/0113828 A1 | 5/2005 | Shields et al. |
| 2005/0203507 A1 | 9/2005 | Truckai et al. |
| 2006/0116675 A1 | 6/2006 | McClurken et al. |
| 2007/0029500 A1 | 2/2007 | Coulombe et al. |
| 2007/0184208 A1 | 8/2007 | Sharma et al. |
| 2008/0050291 A1 | 2/2008 | Nagasawa |
| 2008/0063895 A1 | 3/2008 | Jun et al. |
| 2008/0167398 A1 | 7/2008 | Patil et al. |
| 2009/0102886 A1 | 4/2009 | Sieber et al. |
| 2010/0069904 A1 | 3/2010 | Cunningham |
| 2011/0071596 A1* | 3/2011 | Kara .................... B82Y 30/00 607/57 |
| 2011/0213357 A1 | 9/2011 | Schechter |
| 2011/0270251 A1 | 11/2011 | Horner et al. |
| 2012/0252709 A1 | 10/2012 | Felts et al. |
| 2013/0059273 A1 | 3/2013 | Koo et al. |
| 2013/0116682 A1 | 5/2013 | Koo et al. |
| 2015/0141993 A1 | 5/2015 | Schechter et al. |
| 2017/0119457 A1 | 5/2017 | Sartor et al. |
| 2017/0238991 A1 | 8/2017 | Worrell et al. |

FOREIGN PATENT DOCUMENTS

| | | |
|---|---|---|
| CA | 2520416 A1 | 3/2007 |
| CA | 2609492 A1 | 5/2008 |
| CA | 2626282 A1 | 9/2008 |
| CA | 2934191 A1 | 6/2014 |
| CN | 1649887 A | 8/2005 |
| EP | 0331774 A1 | 9/1989 |
| EP | 0991365 A4 | 4/2000 |
| EP | 3165189 A1 | 5/2017 |
| EP | 3202350 A1 | 8/2017 |
| JP | 62130777 | 6/1987 |
| JP | 03149797 | 6/1991 |
| JP | 8243755 | 9/1996 |
| JP | 2000286094 A | 10/2000 |
| JP | 2001332399 A | 11/2001 |
| JP | 2003093869 A | 4/2003 |
| JP | 2005522824 A | 7/2005 |
| JP | 2005276618 A | 10/2005 |
| JP | 2006114450 A | 4/2006 |
| JP | 2006310101 A | 11/2006 |
| JP | 2007188748 A | 7/2007 |
| JP | 2007207540 A | 8/2007 |
| JP | 2008041495 A | 2/2008 |
| JP | 2008071656 A | 3/2008 |
| WO | 9513313 A1 | 5/1995 |
| WO | 0016706 A1 | 3/2000 |
| WO | 0145862 A1 | 6/2001 |
| WO | 03/085693 A1 | 10/2003 |
| WO | 03/096880 A2 | 11/2003 |
| WO | 2004073490 | 9/2004 |
| WO | 2004094306 A1 | 11/2004 |

(56) References Cited

FOREIGN PATENT DOCUMENTS

| | | |
|---|---|---|
| WO | 2009146432 A1 | 12/2009 |
| WO | 2010008062 A1 | 1/2010 |

OTHER PUBLICATIONS

Australian Examination Report dated Dec. 21, 2018 issued in corresponding AU Appln. No. 2018222882.
Extended European Search Report dated Jan. 30, 2019 issued in corresponding EP Appln. No. 18195879.4.
Extended European Search Report corresponding to European Application No. 09755793.8, dated Jul. 21, 2014; 8 pages.
Japanese Notice of Final Rejection and Denial of Entry of Amendment (with English translation), dated Apr. 2, 2015, corresponding to Japanese Patent Application No. 2012-513022; 10 total pages.
Extended European Search Report issued in Appl. No. 10849146.5 dated Sep. 26, 2013; 6 pages.
Japanese Notice of Final Rejection and Denial of Entry of Amendment (with English translation), dated Jun. 2, 2015, corresponding to Japanese Patent Application No. 2013-502548; 15 total pages.
English translation of Japanese Notice of Reasons for Rejection, dated Feb. 18, 2014, corresponding to Japanese Patent Application No. 2013-502548; 6 pages.
English translation of Japanese Notice of Reasons for Rejection, dated Oct. 7, 2014, corresponding to Japanese Patent Application No. 2013-502548; 6 pages.
Australian Patent Examination Report No. 1, dated Apr. 17, 2014, corresponding to Australian Patent Application No. 2010349784; 3 pages.
European Communication dated Jun. 17, 2014, corresponding to European Patent Application No. 10849146.5; 6 pages.
European Communication/Examination Report dated Jul. 14, 2015, corresponding to European Patent Application No. 09 845 329.3; 8 pages.
European Search Report from Application No. EP 11 00 7711 completed Nov. 4, 2011.
European Search Report from Application No. EP 12191973.2 dated Mar. 20, 2013.
Extended European Search Report from Appl. No. EP 16196104 dated Apr. 7, 2017.
Chinese Office Action issued in Application No. CN 201610972039.9 dated Jul. 31, 2018, together with English language translation (15 pages).
Australian Examination Report dated Feb. 28, 2020 issued in corresponding AU Appln. No. 2019210533.
Partial European Search Report dated Aug. 3, 2020 issued in corresponding EP Appln. No. 20171004.3.
Extended European Search Report dated Dec. 15, 2020 issued in corresponding EP Appln. No. 20171004.3.
Canadian Examination Report dated Jan. 15, 2021 issued in corresponding CA Appln. No. 3,057,667.

* cited by examiner

ELECTROSURGICAL TISSUE SEALING DEVICE WITH NON-STICK COATING

CROSS-REFERENCE TO RELATED APPLICATION

The present application claims the benefit of and priority to U.S. Provisional Patent Application No. 62/561,812, files on Sep. 22, 2017, the entire contents of which is incorporated by reference herein.

BACKGROUND

1. Technical Field

The present disclosure relates to a non-stick coating for an electrosurgical tissue sealing instrument. More particularly, the present disclosure relates to a polymeric organosilicon coating of a controlled thickness disposed on at least a portion of opposing jaw members of an electrosurgical tissue sealing device, the thickness allowing for desired electrical performance while providing tissue sticking reduction.

2. Background of the Related Art

Electrosurgical forceps utilize mechanical clamping action along with electrical energy to effect hemostasis on the clamped tissue. The forceps (open, laparoscopic or endoscopic) include sealing plates which apply energy to the clamped tissue. By controlling the intensity, frequency and duration of the energy applied through the sealing plates to the tissue, the surgeon can cut, coagulate, cauterize, and/or seal tissue.

In the past, efforts have been made to reduce the sticking of soft tissue to the sealing plate during application of energy. In general, such efforts have envisioned non-stick surface coatings, such as polytetrafluoroethylene (PTFE, commonly sold under the trademark TEFLON®) for increasing the lubricity of the tool surface. However, these materials may interfere with the efficacy and efficiency of hemostasis.

SUMMARY

Electrosurgical instruments described herein include at least one tissue sealing plate including a non-stick coating configured to reduce the sticking of soft tissue to the sealing plate during application of energy.

According to an embodiment of the present disclosure, an electrosurgical instrument is provided and includes at least one jaw member having an electrically conductive tissue sealing plate configured to operably couple to a source of electrosurgical energy for treating tissue and a polydimethylsiloxane coating having a thickness of from about 35 nm to about 85 nm disposed on at least a portion of the tissue sealing plate.

In one aspect of the present disclosure, the polydimethylsiloxane coating has a thickness of about 60 nm. In another aspect of the present disclosure, the polydimethylsiloxane coating has a substantially uniform thickness. In another aspect of the present disclosure, the polydimethylsiloxane coating has a non-uniform thickness. In another aspect of the present disclosure, the polydimethylsiloxane coating is discontinuous. In another aspect of the present disclosure, the polydimethylsiloxane coating is continuous. In another aspect of the present disclosure, the electrosurgical instrument also includes an insulative layer disposed on at least a portion of the tissue sealing plate. In another aspect of the present disclosure, the polydimethylsiloxane coating is disposed on at least a portion of each of the pair of opposing jaw members. In another aspect of the present disclosure, the tissue sealing plate is formed of stainless steel.

According to another embodiment of the present disclosure, an electrosurgical instrument is provided and includes a pair of opposing jaw members. Each of the opposing jaw members includes an electrically conductive tissue sealing plate configured to operably couple to a source of electrosurgical energy for treating tissue, a support base configured to support the tissue sealing plate, and an insulative housing configured to secure the tissue sealing plate to the support base. A polydimethylsiloxane coating having a thickness of from about 35 nm to 85 nm is disposed on at least a portion of at least one of the opposing jaw members.

In one aspect of the present disclosure, the polydimethylsiloxane coating is disposed on at least a portion of each of the tissue sealing plates, the support base, and the insulative housing. In another aspect of the present disclosure, the polydimethylsiloxane coating has a thickness of about 60 nm. In another aspect of the present disclosure, the polydimethylsiloxane coating has a substantially uniform thickness. In another aspect of the present disclosure, the polydimethylsiloxane coating has a non-uniform thickness. In another aspect of the present disclosure, the polydimethylsiloxane coating is discontinuous. In another aspect of the present disclosure, the polydimethylsiloxane coating is continuous.

According to another embodiment of the present disclosure, an electrically conductive tissue sealing plate is provided and includes a stainless steel layer having a first surface and an opposing second surface. The stainless steel layer is configured to deliver energy to tissue. An insulative layer is disposed on the second surface of the stainless steel layer and a polydimethylsiloxane coating having a thickness of from about 35 nm to about 85 nm is disposed on at least a portion of the first surface of the stainless steel layer.

In one aspect of the present disclosure, the polydimethylsiloxane coating has a thickness of about 60 nm. In another aspect of the present disclosure, the polydimethylsiloxane coating has a non-uniform thickness. In another aspect of the present disclosure, the polydimethylsiloxane coating is discontinuous.

According to another embodiment of the present disclosure, a method of inhibiting tissue from sticking to an electrically conductive component of an electrosurgical tissue sealing device during application of energy to tissue is provided. The method includes applying a polydimethylsiloxane coating on at least a portion of an electrically conductive component of an electrosurgical tissue sealing device using a plasma enhanced chemical vapor deposition technique. The method also includes controlling a thickness of the polydimethylsiloxane coating applied to be from about 35 nm to about 85 nm.

According to another embodiment of the present disclosure, an electrosurgical instrument is provided and includes a pair of jaw members each having an electrically conductive tissue sealing plate configured to operably couple to a source of electrosurgical energy. The tissue sealing plates are configured to deliver electrosurgical energy to tissue based on at least one sensed tissue parameter. The electrosurgical instrument also includes a non-stick coating disposed on at least a portion of each of the tissue sealing plates. The non-stick coating has a thickness controlled to reduce sticking of the tissue to the electrically conductive sealing plates during delivery of electrosurgical energy to the tissue and to permit a sensing of the at least one tissue parameter.

In one aspect of the present disclosure, the non-stick coating may be formed from a pre-cursor feedstock including hexamethyldisiloxane, tetramethylsilane, hexamethyldisilazane, or combinations thereof. In another aspect of the present disclosure, the polymethyldisloxane non-stick coating has a thickness of from about 35 nm to about 85 nm. In another aspect of the present disclosure, the non-stick coating has a thickness of about 60 nm. In another aspect of the present disclosure, the least one tissue parameter is selected from the group consisting of temperature and impedance.

According to another embodiment of the present disclosure, a method of inhibiting tissue from sticking to an electrically conductive component of an electrosurgical tissue sealing device during application of energy to tissue is provided. The method includes applying a non-stick coating on at least a portion of an electrically conductive component of an electrosurgical tissue sealing device using a plasma enhanced chemical vapor deposition technique and controlling a thickness of the non-stick coating applied to inhibit tissue from sticking to the electrically conductive component during application of energy to the tissue and to permit sensing of at least one tissue parameter generated via application of energy to the tissue.

In one aspect of the present disclosure, the method also includes controlling the thickness of the non-stick coating to be from about 35 nm to about 85 nm. In another aspect of the present disclosure, the non-stick coating includes hexamethyldisiloxane. In another aspect of the present disclosure, the method also includes controlling the thickness of the non-stick coating to be about 60 nm.

According to another embodiment of the present disclosure, an electrosurgical system is provided and includes an electrosurgical energy source and an electrosurgical instrument configured to couple to the electrosurgical energy source. The electrosurgical instrument includes a pair of opposing jaw members configured to grasp tissue and a pair of electrically conductive tissue sealing plates coupled respectively to the pair of opposing jaw members. The pair of sealing plates are configured to deliver electrosurgical energy to tissue and the electrosurgical generator is configured to sense at least one tissue parameter generated by the delivery of electrosurgical energy to the tissue via the sealing plates. The electrosurgical instrument also includes a non-stick coating disposed on at least a portion of each of the tissue sealing plates. The non-stick coating has a thickness controlled to reduce sticking of the tissue to the electrically conductive sealing plate and to permit sensing of the at least one tissue parameter.

In one aspect of the present disclosure, the non-stick coating may be formed from a pre-cursor feedstock including hexamethyldisiloxane, tetramethylsilane, hexamethyldisilazane, or combinations thereof. In another aspect of the present disclosure, the non-stick coating has a thickness of from about 35 nm to about 85 nm. In another aspect of the present disclosure, the non-stick coating has a thickness of about 60 nm. In another aspect of the present disclosure, the at least one tissue parameter is selected from the group consisting of temperature and impedance.

According to one embodiment of the present disclosure a method for applying a coating on at least a portion of an electrically conductive component of an electrosurgical tissue sealing device is disclosed. The method includes: placing the electrically conductive component into a plasma deposition chamber; supplying an ionizable media into the plasma deposition chamber; igniting the ionizable media to generate a first plasma at a first power level to prepare the electrically conductive component to receive the coating; supplying the ionizable media and a precursor composition into the plasma deposition chamber; and igniting the ionizable media and the precursor composition to generate a second plasma at a second power level thereby forming the coating on the electrically conductive component.

Implementations of the above embodiment may include one or more of the following features, where the ionizable media is oxygen and the precursor composition is hexamethyldisiloxane. The method may also include controlling at least one of ratio of the ionizable media and the precursor composition, duration of the second plasma, or the second power level to adjust thickness of the coating.

According to another embodiment of the present disclosure an electrosurgical system is disclosed. The system includes: an electrosurgical instrument including at least one electrically conductive component having a non-stick coating and a storage medium storing data pertaining to the non-stick coating; an electrosurgical generator configured to generate electrosurgical energy to the at least one electrically conductive component, the electrosurgical generator including: a reader configured to interface with the storage medium and read the data; and a controller coupled to the reader and configured to adjust at least one parameter of the electrosurgical energy based on the data. Other embodiments of this aspect include corresponding computer systems, apparatus, and computer programs recorded on one or more computer storage devices, each configured to perform the actions of the methods.

Implementations of the above embodiment may include one or more of the following features. The electrosurgical generator may further include a memory storing an algorithm for controlling the electrosurgical energy. The algorithm parameter may be a treatment completion threshold. The data may include a thickness of the non-stick coating. Implementations of the described techniques may include hardware, a method or process, or computer software on a computer-accessible medium.

According to another embodiment of the present disclosure a method for reprocessing a coated electrosurgical device is disclosed. The method includes: removing a coating by placing an electrically conductive component of an electrosurgical device into a plasma deposition chamber; supplying a first ionizable media into the plasma deposition chamber; and igniting the first ionizable media to generate a first plasma at a first power level to remove a previously-used coating from the electrically conductive component. The method further includes reapplying a new coating by supplying a second ionizable media into the plasma deposition chamber; igniting the second ionizable media to generate a second plasma at a second power level to prepare the electrically conductive component to receive a new coating; supplying the second ionizable media and a precursor composition into the plasma deposition chamber; and igniting the second ionizable media and the precursor composition to generate a third plasma at a third power level thereby forming the new coating on the electrically conductive component.

According to one aspect of the above embodiment, the first ionizable media is tetrafluoromethane, the second ionizable media is oxygen, and the precursor composition is hexamethyldisiloxane, tetramethylsilane, hexamethyldisilazane, or combinations thereof.

BRIEF DESCRIPTION OF THE DRAWINGS

The above and other aspects, features, and advantages of the present electrosurgical tissue sealing instruments will become more apparent in light of the following detailed description when taken in conjunction with the accompanying drawings in which.

DETAILED DESCRIPTION

Figure 1:
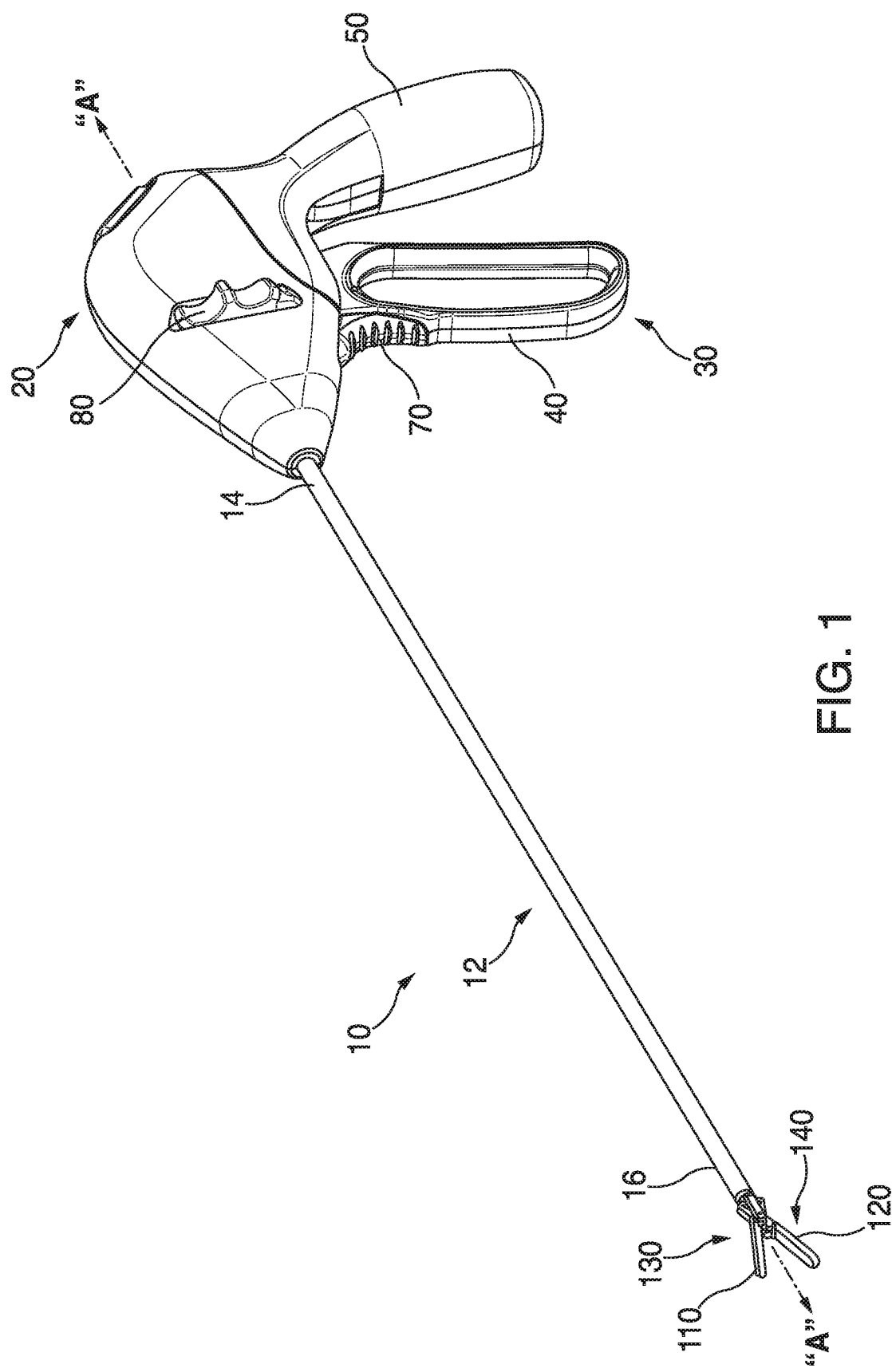
FIG. 1 is a perspective view of a laparoscopic bipolar forceps in accordance with an aspect of the present disclosure.

Particular aspects of the present electrosurgical tissue sealing instruments are described herein below with reference to the accompanying drawings; however, it is to be understood that the disclosed aspects are merely examples of the disclosure and may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the concepts of the present disclosure in virtually any appropriately detailed structure.

Like reference numerals may refer to similar or identical elements throughout the description of the figures. As shown in the drawings and described throughout the following description, as is traditional when referring to relative positioning on a surgical instrument, the term "proximal" refers to the end of the apparatus which is closer to the user and the term "distal" refers to the end of the apparatus which is further away from the user. The term "clinician" refers to any medical professional (i.e., doctor, surgeon, nurse, or the like) performing a medical procedure involving the use of aspects described herein.

As described in more detail below with reference to the accompanying figures, the present disclosure is directed to electrosurgical instruments having a non-stick coating disposed on one or more components (e.g., tissue sealing plates, jaw members, electrical leads, insulators etc.) The thickness of the non-stick coating is carefully controlled, allowing for desired electrical performance while providing tissue sticking reduction during tissue sealing.

Any material capable of providing the desired functionality (namely, reduction of tissue sticking while simultaneously maintaining sufficient electrical transmission to permit tissue sealing) may be used as the non-stick coating, provided it has adequate biocompatibility. The material may be porous to allow for electrical transmission. Among such materials are silicone and silicone resins that can be applied using a plasma deposition process to precisely control thickness, and can withstand the heat generated during tissue sealing. Silicone resins suitable for the non-stick coating include, but are not limited to, polydimethyl siloxanes, polyester-modified methylphenyl polysiloxanes, such as polymethylsilane and polymethylsiloxane, and hydroxyl functional silicone resins. In some embodiments, the non-stick coating is made from a composition including a siloxane, which may include hexamethyldisiloxane, tetramethylsilane, hexamethyldisilazane, or combinations thereof.

In some embodiments, the non-stick coating is a polydimethylsiloxane coating formed by plasma-enhanced chemical vapor deposition ("PECVD") of hexamethyldisiloxane ("HMDSO"). Advantageously, the polydimethylsiloxane coating operates to reduce the sticking of tissue to the sealing plates and/or the entire jaw member. Additionally, the polydimethylsiloxane coating may operate to reduce the pitting of the sealing plates and may provide durability against electrical and/or mechanical degradation of the sealing plates and the jaw members, as a whole.

In some embodiments, opposing jaw members of an electrosurgical vessel sealing instrument (see FIGS. 1 and 2) include electrically conductive tissue sealing plates on which the non-stick coating is directly deposited. The application of the non-stick coating may be accomplished using any system and process capable of precisely controlling the thickness of the coating. In some embodiments, HMDSO is deposited on the sealing plates using plasma enhanced chemical vapor deposition (PECVD) or other suitable methods such as atmospheric pressure plasma enhanced chemical vapor deposition (AP-PECVD). For example, the application of the polydimethylsiloxane coating may be accomplished using a system and process that includes a plasma device coupled to a power source, a source of liquid and/or gas ionizable media (e.g., oxygen), a pump, and a vacuum chamber. One such illustrative system and process is described in commonly-owned U.S. Patent Application Publication No. US 2013/0116682, the entire contents of which are incorporated herein by reference. The power source may include any suitable components for delivering power or matching impedance to the plasma device. More particularly, the power source may be any radio frequency generator or other suitable power source capable of producing electrical power to ignite and sustain the ionizable media to generate a plasma effluent.

The thickness of the non-stick coating affects the non-stick performance of the sealing plates and may affect the tissue sealing performance of the sealing plates as well. For example, if the non-stick coating is too thick, the tissue sealing performance of the sealing plates may be negatively affected. More specifically, a non-stick coating above a particular thickness (e.g., greater than about 200 nm) may create a uniform dielectric barrier or surface impedance on the sealing plates, which may negatively impact the effectiveness of tissue sensing algorithms employed by an electrosurgical generator that controls the delivery of electrosurgical energy to the vessel sealing instrument based on sensed tissue parameters (e.g., impedance, temperature, etc.) generated by the application of electrosurgical energy to the tissue via the sealing plates. If the applied non-stick coating is too thin (e.g., less than about 20 nm), the non-stick coating may not provide adequate tissue sticking reduction.

Embodiments of the present disclosure provide for disposing a non-stick coating on components of a vessel sealing instrument (e.g., sealing plates, jaw members, electrical leads, insulators, etc.) at a particular thickness or within a particular range of thicknesses such that the non-stick coating provides adequate tissue sticking reduction during tissue sealing without negatively impacting tissue sealing performance of the vessel sealing instrument.

In some embodiments, a polydimethylsiloxane coating may be applied to a portion of the electrosurgical device at a thickness from about 20 nm to about 200 nm, in embodiments, the coating may be from about 25 nm to about 120 nm, and in further embodiments, from about 35 nm to about 85 nm. In a particular embodiment, the non-stick coating may be about 60 nm thick. In some embodiments, the thickness of the non-stick coating may vary such that the non-stick coating has a substantially non-uniform thickness. For example, a first portion of the non-stick coating may be about 60 nm thick and any one or more other portions of the non-stick coating may have a thickness other than about 60 nm but within the range of about 20 nm to about 200 nm, in embodiments within the range of from about 25 nm to about 120 nm, and in further embodiments, from about 35 nm to about 85 nm. In other embodiments, the non-stick coating has a substantially uniform thickness. Without wishing to be bound by any particular theory, it is believed that polydimethylsiloxane coatings in the foregoing range do not provide a complete surface seal, and that it is the lack of a complete uniform seal over the surface at these controlled thicknesses that allows the electrical algorithms of certain electrosurgical generators to perform properly. One such electrosurgical generator employing a tissue sensing algorithm is described in U.S. Pat. No. 9,603,752, the entire contents of which are incorporated herein by this reference. Those skilled in the art reviewing the present disclosure will readily envision other electrosurgical generators employing other algorithms.

In some embodiments, the thickness of the non-stick coating is about 0.01% of the thickness of the sealing plate.

Turning now to FIG. 1, an instrument generally identified as forceps 10 is for use with various surgical procedures and includes a housing 20, a handle assembly 30, a rotating assembly 80, a trigger assembly 70, and an end effector 130 that mutually cooperate to grasp, seal, and divide tubular vessels and vascular tissues. Forceps 10 includes a shaft 12 extending from a distal end of the housing 20. The shaft 12 has a distal end 16 configured to mechanically engage the end effector 130 and a proximal end 14 that mechanically engages the housing 20.

The end effector 130 includes opposing jaw members 110 and 120, which cooperate to effectively grasp tissue for sealing purposes. Both jaw members 110 and 120 pivot relative to one another about a pivot pin (not shown). Alternatively, the forceps 10 may include a jaw member 110 movable relative to a stationary jaw member 120, and vice versa. The jaw members 110 and 120 may be curved to facilitate manipulation of tissue and to provide better "line-of-sight" for accessing targeted tissues. A sensor 140 may be disposed on or proximate to at least one of the jaw members 110 and 120 for sensing tissue parameters (e.g., temperature, impedance, etc.) generated by the application of electrosurgical energy to tissue via the jaw members 110 and 120. The sensor 140 may include a temperature sensor, tissue hydration sensor, impedance sensor, optical clarity sensor, jaw gap sensor, strain and/or force sensor, or the like. Through a cable (not shown) coupling the forceps 10 to an electrosurgical generator (not shown), sensed tissue parameters may be transmitted as data to the electrosurgical generator having suitable data processing components (e.g., microcontroller, memory, sensor circuitry, etc.) for controlling delivery of electrosurgical energy to the forceps 10 based on data received from the sensor 140.

Examples of forceps are shown and described in U.S. Patent Application Publication No. 2013/0296922 and U.S. Pat. No. 9,655,673, the entire contents of each of which are incorporated herein by reference.

Figure 2:
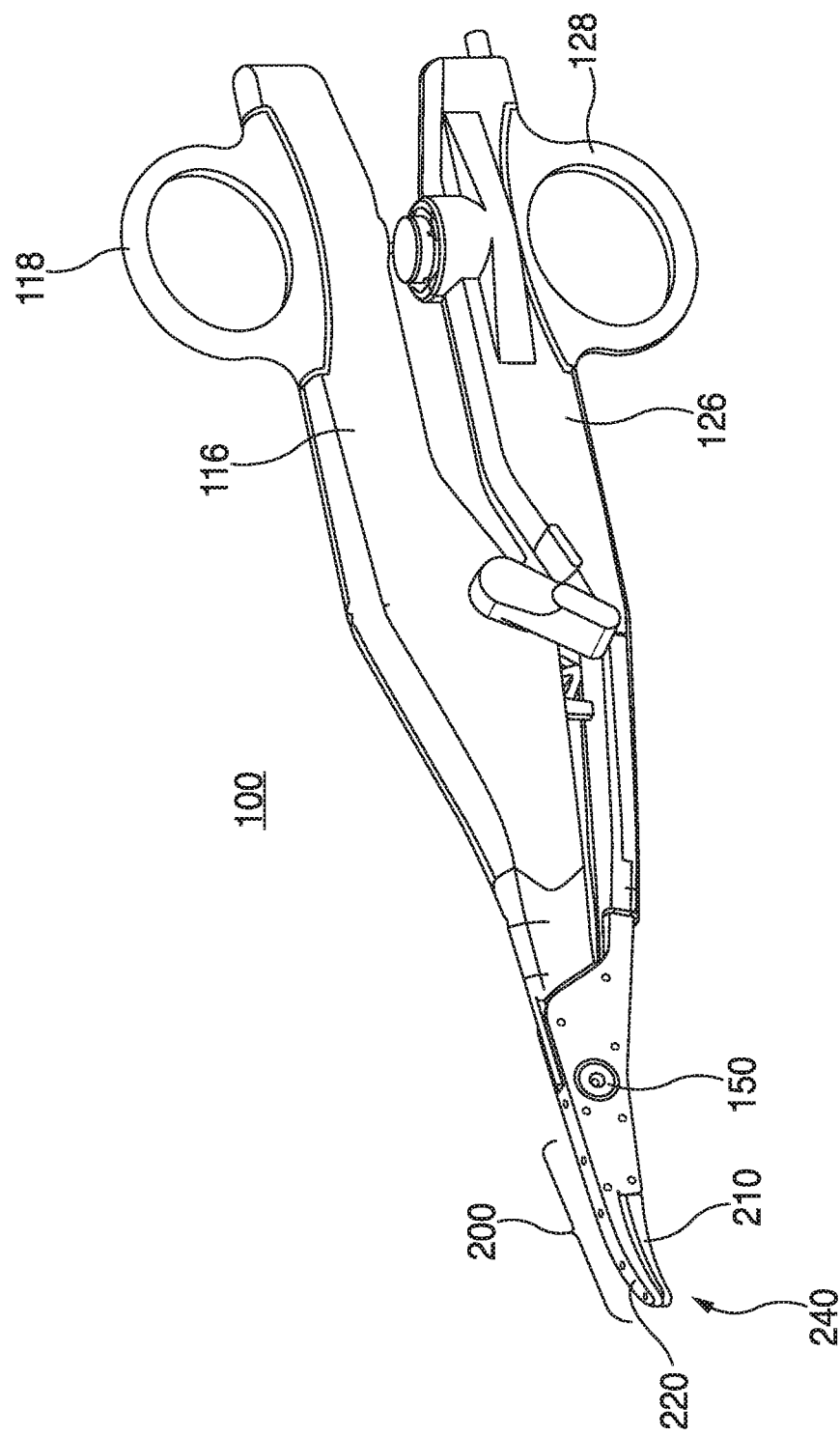
FIG. 2 is a perspective view of an open bipolar forceps according to an aspect of the present disclosure.

With regard to FIG. 2, an open forceps 100 for use with various surgical procedures is shown. The forceps 100 includes a pair of opposing shafts 116 and 126 having an end effector 200 disposed at a distal end of the shafts 116, 126. The end effector 200 includes pair of opposing jaw members 210 and 220 that are connected about a pivot member 150 and that are movable relative to one another to grasp tissue. Each shaft 116 and 126 includes a handle 118 and 128, respectively, to facilitate movement of the shafts 116 and 126 relative to one another to pivot the jaw members 210 and 220 between an open position, wherein the jaw members 210 and 220 are disposed in spaced relation relative to one another, and a closed position, wherein the jaw members 210 and 220 cooperate to grasp tissue there between. Similar to the forceps 10 shown in FIG. 1, a sensor 240 may be disposed on or proximate to at least one of the jaw members 210 and 220 of the forceps 100 for sensing tissue parameters (e.g., temperature, impedance, etc.) generated by the application of electrosurgical energy to tissue via the jaw members 210 and 220. The sensor 240 may include a temperature sensor, tissue hydration sensor, impedance sensor, optical clarity sensor, or the like. Through a cable (not shown) coupling the forceps 100 to an electrosurgical generator (not shown), sensed tissue parameters may be transmitted as data to the electrosurgical generator having suitable data processing components (e.g., microcontroller, memory, sensor circuitry, etc.) for controlling delivery of electrosurgical energy to the forceps 100 based on data received from the sensor 240.

Figure 3A:
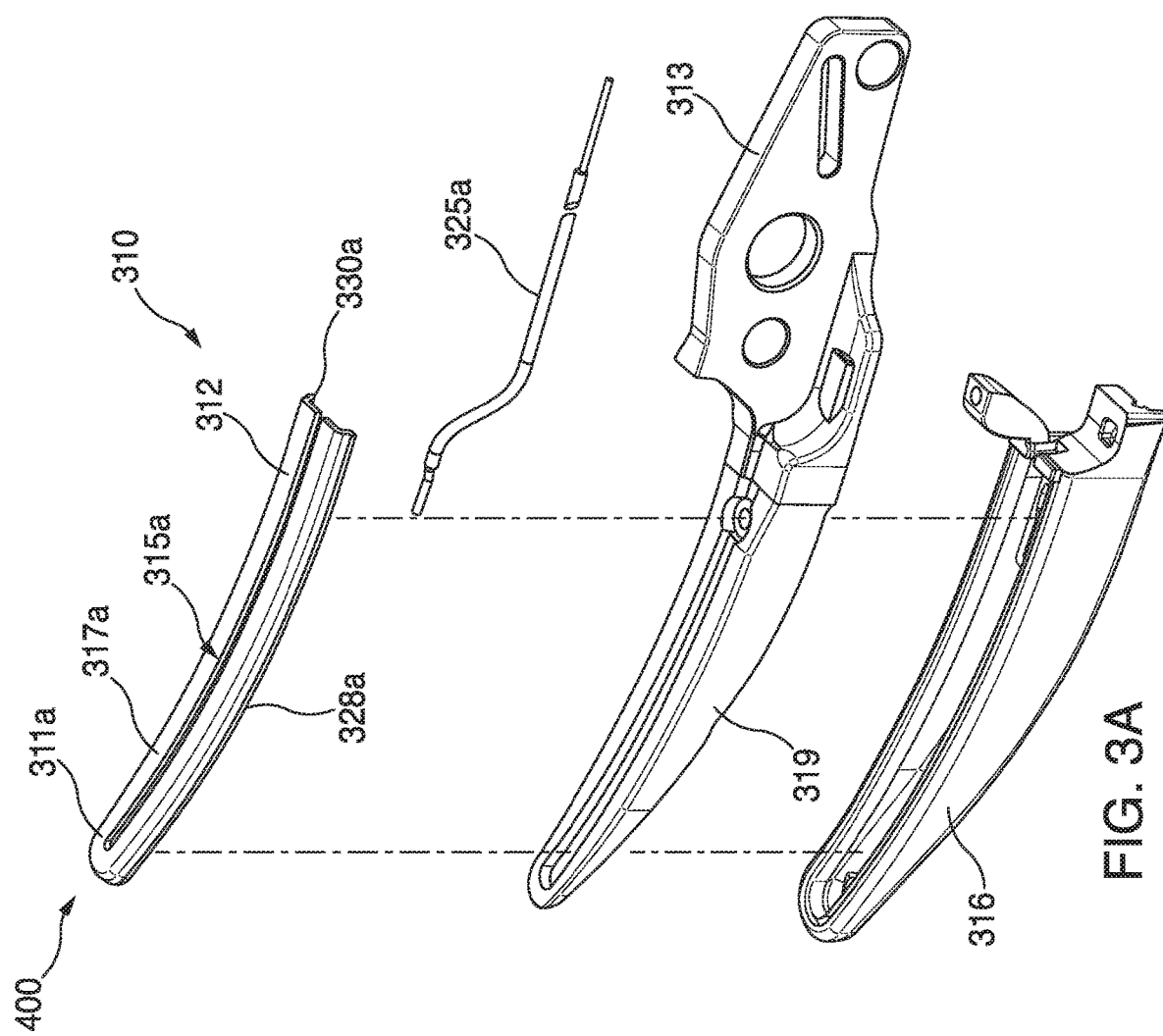
FIGS. 3A and 3B are exploded views of opposing jaw members according to an aspect of the present disclosure.
Figure 3B:
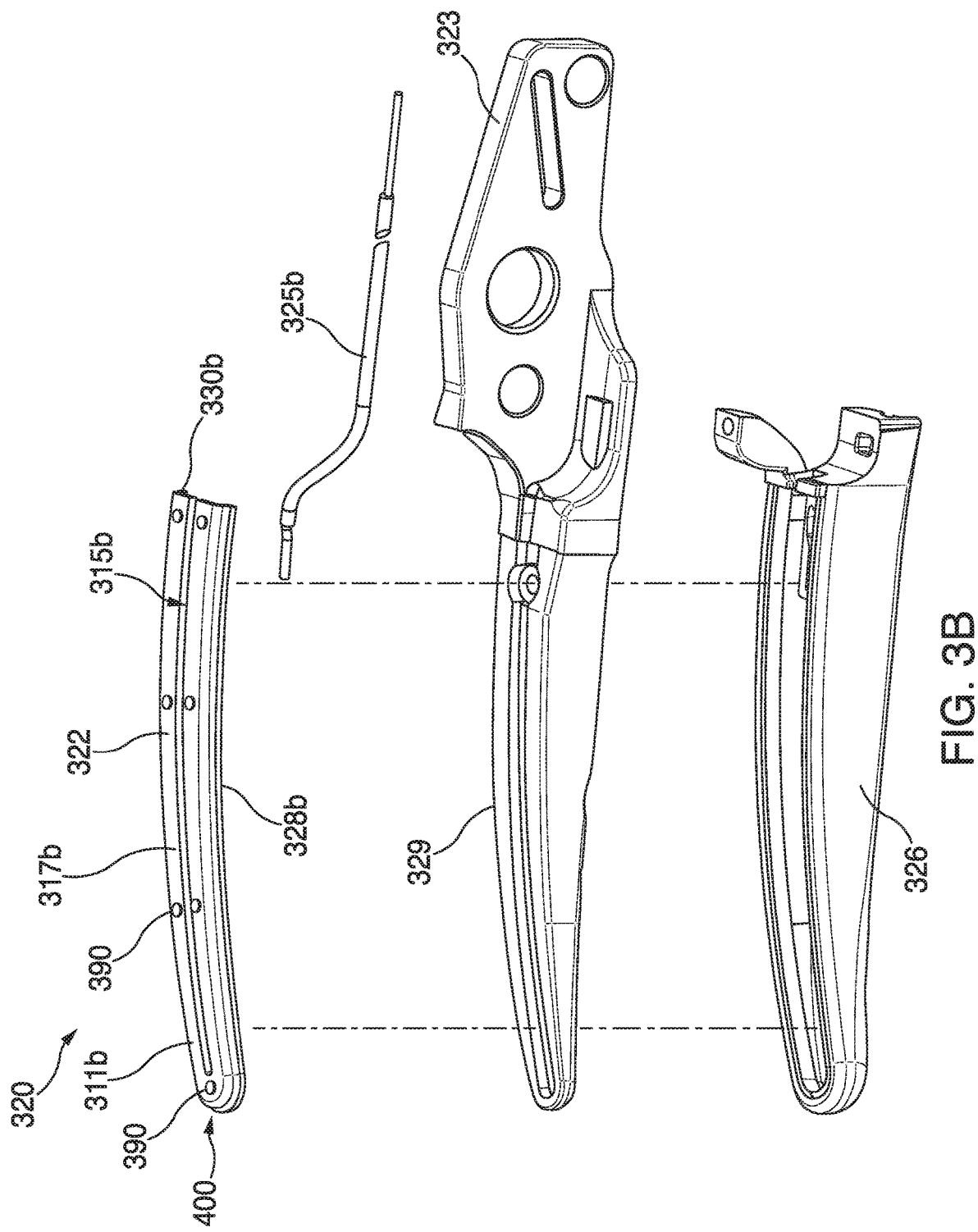

FIGS. 3A and 3B show perspective views of the jaw members 310 and 320, respectively, according to an embodiment of the present disclosure. The jaw members 310 and 320 may be utilized with the endoscopic forceps 10 (FIG. 1) or the open forceps 100 (FIG. 2) and operate similarly as described above with respect to the jaw members 110 and 120 (FIG. 1) and the jaw members 210 and 220 (FIG. 2). Each of the jaw members 310 and 320 include: sealing plates 312 and 322, respectively; electrical leads 325a and 325b, respectively; and support bases 319 and 329 that extend distally from flanges 313 and 323, respectively.

Each of the sealing plates 312 and 322 include an underside 328a and 328b, respectively, that may include a respective electrically insulative layer 330a and 330b bonded thereto or otherwise disposed thereon. The electrically insulative layers 330a and 330b operate to electrically insulate the sealing plates 312 and 322, respectively, from the support bases 319 and 329, respectively. Further, the electrically insulative layers 330a and 330b operate to prevent or slow the onset of corrosion of the sealing plates 312 and 322, respectively, at least on the undersides 328a, 328b thereof. In one embodiment, the electrically insulative layers 330a and 330b may be formed from polyimide. However, in other embodiments, any suitable electrically insulative material may be utilized, such as polycarbonate, polyethylene, etc.

Additionally, each of the jaw members 310 and 320 include an outer surface 311a and 311b, respectively, that includes a non-stick (e.g., polydimethylsiloxane) coating 400 disposed thereon. The non-stick coating 400 may be disposed on selective portions of either of the jaw members 310 and 320, or may be disposed on the entire outer surfaces 311a and 311b. In some embodiments, the non-stick coating 400 is disposed on a tissue-engaging surface 317a and 317b of the sealing plates 312 and 322, respectively. The non-stick coating 400 operates to reduce the sticking of tissue to the sealing plates 312 and 322, the jaw members 310 and 320, the electrical leads 325a and 325b, and/or the surrounding insulating material.

The support bases 319 and 329 are configured to support the sealing plates 312 and 322 thereon. The sealing plates 312 and 322 may be affixed atop the support bases 319 and 329, respectively, by any suitable method including but not limited to snap-fitting, overmolding, stamping, ultrasonic welding, laser welding, etc. The support bases 319 and 329 and the sealing plates 312 and 322 are at least partially encapsulated by insulative housings 316 and 326, respectively, by way of an overmolding process to secure sealing plates 312 and 322 to support bases 319 and 329, respectively. The sealing plates 312 and 322 are coupled to electrical leads 325a and 325b, respectively, via any suitable method (e.g., ultrasonic welding, crimping, soldering, etc.). The electrical leads 325a and 325b serve to deliver electrosurgical energy (e.g., from an electrosurgical energy generator) to the sealing plates 312 and 322, respectively. More specifically, electrical lead 325a supplies a first electrical potential to sealing plate 312 and electrical lead 325b supplies a second electrical potential to opposing sealing plate 322.

Jaw member 320 (and/or jaw member 310) may also include a series of stop members 390 disposed on the tissue-engaging surface 311b of the sealing plate 322 to facilitate gripping and manipulation of tissue and to define a gap between the jaw members 310 and 320 during sealing and cutting of tissue. The series of stop members 390 may be disposed (e.g., formed, deposited, sprayed, affixed, coupled, etc.) onto the sealing plate 322 during manufacturing. Some or all of the stop members 390 may be coated with the non-stick coating 400 or, alternatively, may be disposed on top of the non-stick coating 400.

The sealing plates 312 and 322 may include longitudinal knife slots 315a and 315b, respectively, defined there through and configured to receive a knife blade (not shown) that reciprocates through the knife slots 315a and 315b to cut tissue. The electrically insulative layers 330a and 330b disposed on the respective undersides 328a and 328b of sealing plates 312 and 322, respectively, allow for various blade configurations such as, for example, T-shaped blades or I-shaped blades that may contact the underside of the sealing plate (and/or insulating layer) during reciprocation through knife slots 315a, 315b. That is, the electrically insulative layers 330a, 330b operate to protect both the knife blade and the undersides 328a and 328b of the sealing plates 312 and 322, respectively, from damage or wearing. Further, in the instance that an electrically conductive knife blade is utilized (e.g., for electric tissue cutting), the electrically insulative layers 330a, 330b help to electrically insulate the sealing plates 312, 322 from the electrically conductive knife blade.

Figure 4A:
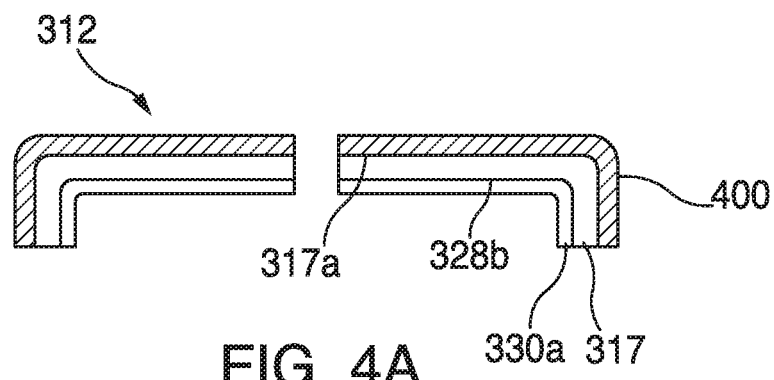
FIG. 4A is a front cross sectional view of a sealing plate according to an aspect of the present disclosure.

Turning now to FIG. 4A, a front cross sectional view of sealing plate 312 is shown and will be described. Sealing plate 312 has a stainless steel layer 317, a non-stick coating 400, and, optionally, an electrically insulative layer 330a disposed on the underside 328b of the stainless steel layer 317. The non-stick coating 400 may be applied to at least the outer surface 311a of the stainless steel layer 317. Bonding electrically insulative layer 330a to stainless steel layer 317 may be accomplished by any suitable method including, but not limited to, applying adhesive between electrically insulative layer 330a and stainless steel layer 317, using heat treatment to bond electrically insulative layer 330a to stainless steel layer 317, and/or any combinations thereof. The optional electrically insulative layer 330a may have a thickness ranging from about 0.0005 inches to about 0.01 inches.

The non-stick coating 400 may be discontinuous or continuous. In some embodiments, the discontinuity or continuity of the non-stick coating 400 may depend on the thickness of the non-stick coating 400. In some embodiments, the non-stick coating may be continuous over the entire sealing plate 312, thereby hermetically sealing the sealing plate 312. In some embodiments, the non-stick coating may be discontinuous over the entire sealing plate 312. The discontinuous non-stick coating may be applied intermittently on the sealing plate 312 using a suitable discontinuous-coating or patch-coating process. The patchiness of the discontinuous non-stick coating may allow the thickness of the discontinuous non-stick coating to be increased relative to a continuous non-stick coating while maintaining adequate non-stick performance and tissue sealing performance.

In some embodiments, the sealing plate 312 may be formed by bonding a sheet of electrically insulative material to a sheet of stainless steel and coating the sheet of stainless steel with a non-stick coating. Once the two materials are bonded together, and the stainless steel sheet is coated with the non-stick layer 400, sealing plate 312 may be formed by stamping, machining, or any other suitable method used to form a sealing plate.

In some embodiments, the sealing plate 312 may first be formed by stamping, machining, or any other suitable method used to form a sealing plate. Once the sealing plate 312 is formed, the non-stick layer 400 is applied to the sealing plate 312 prior to assembling jaw member 310. Once the sealing plate 312 is coated with the non-stick layer 400, the sealing plate 312 may be affixed atop the support base 319, secured to the support base 319 via the insulative housing 316, and coupled to the electrical lead 325a as described above with respect to FIG. 3A to form the jaw member 310. Optionally, once the jaw member 310 is formed, a non-stick coating may be applied to the other components of the jaw member 310 (e.g., the support base 319, the insulative housing 316, the electrical lead 325a, etc.). In some embodiments, a non-stick coating may be applied to other components of forceps 10 (FIG. 1) or forceps 100 (FIG. 2) to reduce frictional sticking associated with operation of these devices. For example, a non-stick coating may be applied to the shaft 12 of forceps 10, to the pivot member 150 and opposing shafts 116 and 126 of forceps 100, and/or to a knife (not shown) used with either of forceps 10 or forceps 100.

Figure 4B:
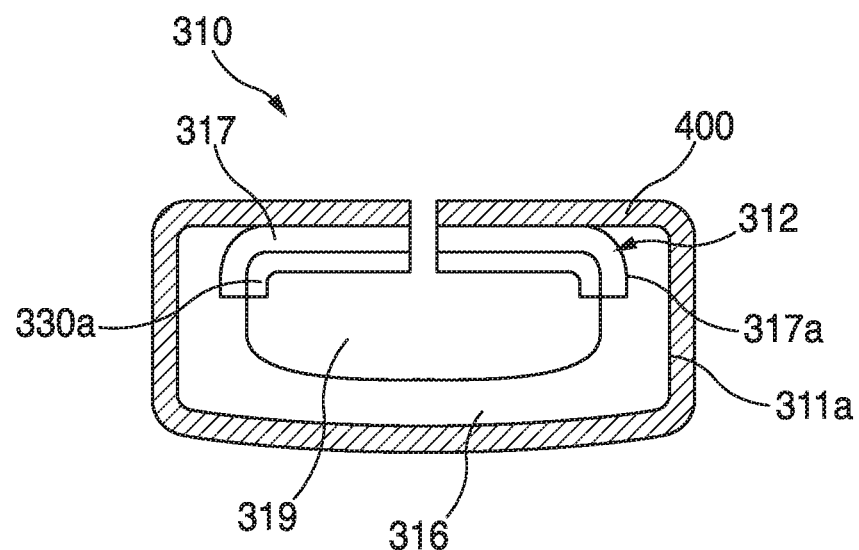
FIG. 4B is a front cross sectional view of a jaw member according to an aspect of the present disclosure.

Turning now to FIG. 4B, a front cross sectional view of jaw member 310 is shown and will be described. Jaw member 310 includes sealing plate 312 having a stainless steel layer 317 and, optionally, an electrically insulative layer 330a. Sealing plate 312 is affixed to support base 319 via any suitable process. Additionally, with sealing plate 312 secured to support base 319, the combined sealing plate 312 and support base 319 is secured to insulative housing 316 via any suitable process. A non-stick coating 400 is applied to the outer surface 311a of the assembled sealing plate 312, the support base 319, the insulative housing 316, and, optionally the electrical lead 325a (FIG. 3A). In some embodiments it may be useful to partially coat the outer surface 311a of the jaw member 310 or include thicker layers of the non-stick coating 400 on different portions of the outer surface 311a of the jaw member 310.

Additionally or alternatively, in some embodiments, the sealing plate 312 may be coated with the non-stick coating 400 in the manner described above with respect to FIG. 4A and the outer surface 311a of the jaw member 310 may also be coated with the non-stick coating 400.

Once the non-stick coating 400 is disposed on the sealing plates 312 and 322 and/or the jaw member 310, which may be assembled with an opposing jaw member (e.g., pivotably coupled) to form an end effector (e.g., end effector 130 or end effector 200). In some embodiments, the non-stick coating 400 may be disposed on the sealing plates 312 and 322 and/or the jaw member 310 subsequent to assembly of the end effector.

In some embodiments, a polydimethylsiloxane coating at the above-described thickness or within the above-described range of thicknesses may be combined with one or more additional coatings. For example, the one or more coatings may be disposed directly on the stainless steel layer of the sealing plate prior to the polydimethylsiloxane coating being deposited such that the polydimethylsiloxane coating is disposed directly on the one or more coatings and not directly on the stainless steel layer of the sealing plate. For example, U.S. Publication No. 2017/0119457 describes a vessel sealing instrument having sealing plates with a HMDSO-based coating disposed over a chromium nitride ("CrN") coating.

Figure 5:
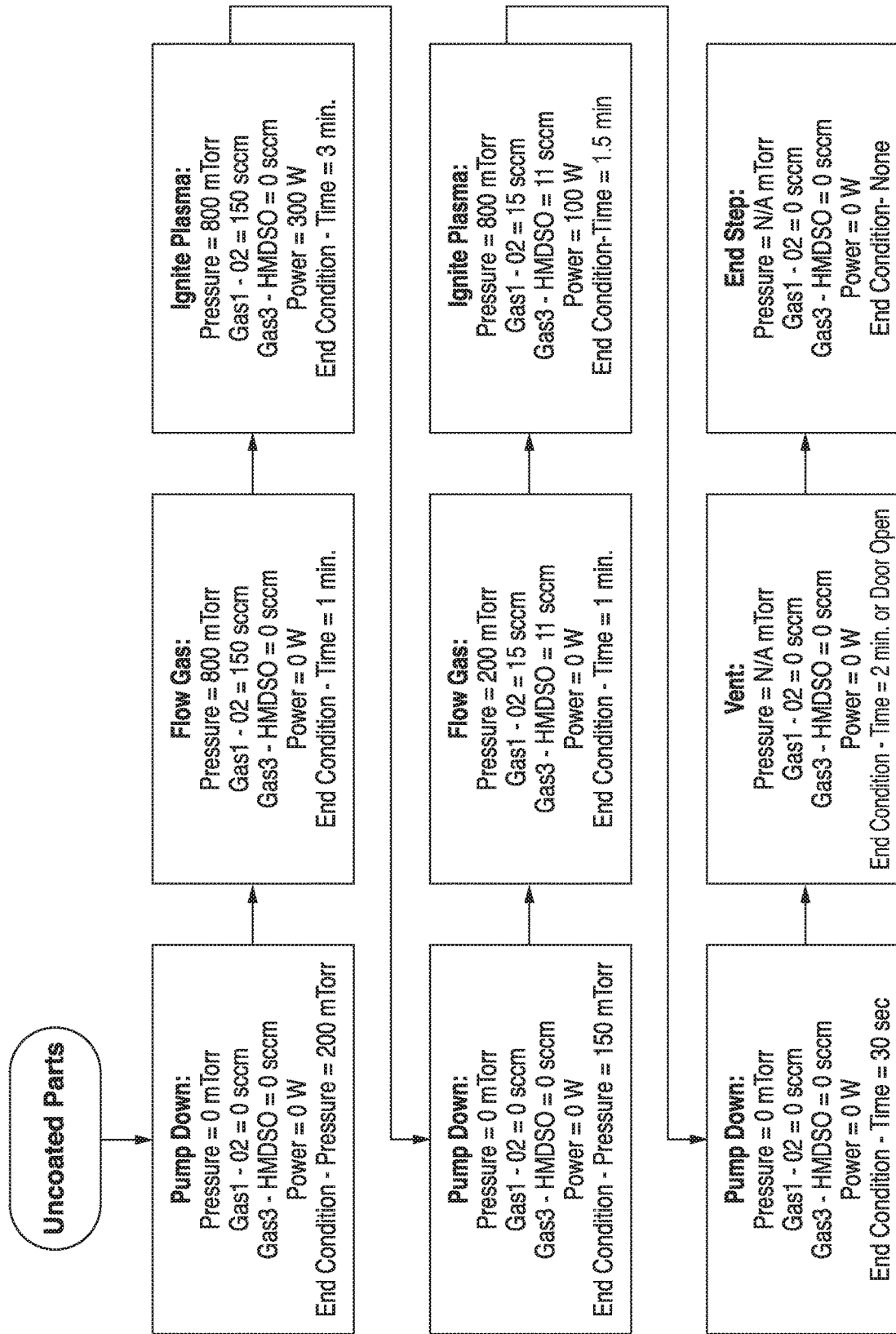
FIG. 5 is a flow chart of a method for applying a non-stick coating to the jaw members according to an aspect of the present disclosure.

With reference to FIG. 5, a flow chart illustrating a method for forming the non-stick coating 400 is disclosed. It is envisioned that any suitable chemical vapor deposition or plasma vacuum system may be used to perform the method, such as the system disclosed in U.S. Pat. No. 8,187,484, the ION 140 Plasma System available from PVA TEPLA AG of Wettenberg, Germany, and the like.

Uncoated jaw members (e.g., jaw members 310) are loaded into a vacuum plasma deposition chamber of a plasma system. The chamber is then pumped down to form a vacuum within the chamber. After the vacuum is established, ionizable media, such as, oxygen is supplied into the chamber at any suitable rate until a set point pressure is reached. Oxygen flow rate may be from about 100 standard cubic centimeters per minute (SCCM) to about 1,000 SCCM, in embodiments, flow rate may be about 150 SCCM. Set point pressure may be from 600 mTorr to about 1,000 mTorr, in embodiments, the pressure may be 800 mTorr. Once the desired pressure is reached, oxygen plasma is ignited for a first period of time at a first power level to prepare the surface for coating. The first time period may be about 3 minutes and the first power level may be 300 watts. Oxygen-based plasma removes residual organic impurities and weakly bound organic contamination from the jaw members. It also prepares surfaces for subsequent processing (e.g., application of the non-stick coating 400) and improves surface coverage and enhance adhesion of the non-stick coating 400.

After oxygen-based plasma application is completed, the chamber is pumped down again until vacuum is established. Into the vacuumed chamber, oxygen and the precursor material for forming the non-stick coating 400, such as, hexamethyldisiloxane, tetramethylsilane, hexamethyldisilazane, are supplied at their respective flow rates until a set point pressure is reached. Oxygen flow rate may be from about 10 SCCM to about 50 SCCM, in embodiments, the flow rate may be about 15 SCCM. Organosilicon precursor flow rate may be from about 10 SCCM to about 50 SCCM, in embodiments, the flow rate may be about 11 SCCM. Set point pressure may be from about 100 mTorr to about 500 mTorr, in embodiments, set point pressure may be about 200 mTorr. Once the desired pressure is reached, plasma is ignited for a second period of time at a second power level. The second time period may be about 1.5 minutes and the second power level may be 100 watts. The chamber is then is pumped down again and vented. At this stage of the process the non-stick coating 400 is formed. In particular, as the precursor is polymerized, polydimethylsiloxane forms the non-stick coating 400. The thickness of the non-stick coating 400 may be adjusted by controlling one or more of the following parameters, including but not limited to, ratio of gases (e.g., oxygen and organosilicon precursor), duration of plasma application, and power for ionizing gases.

Figure 6:
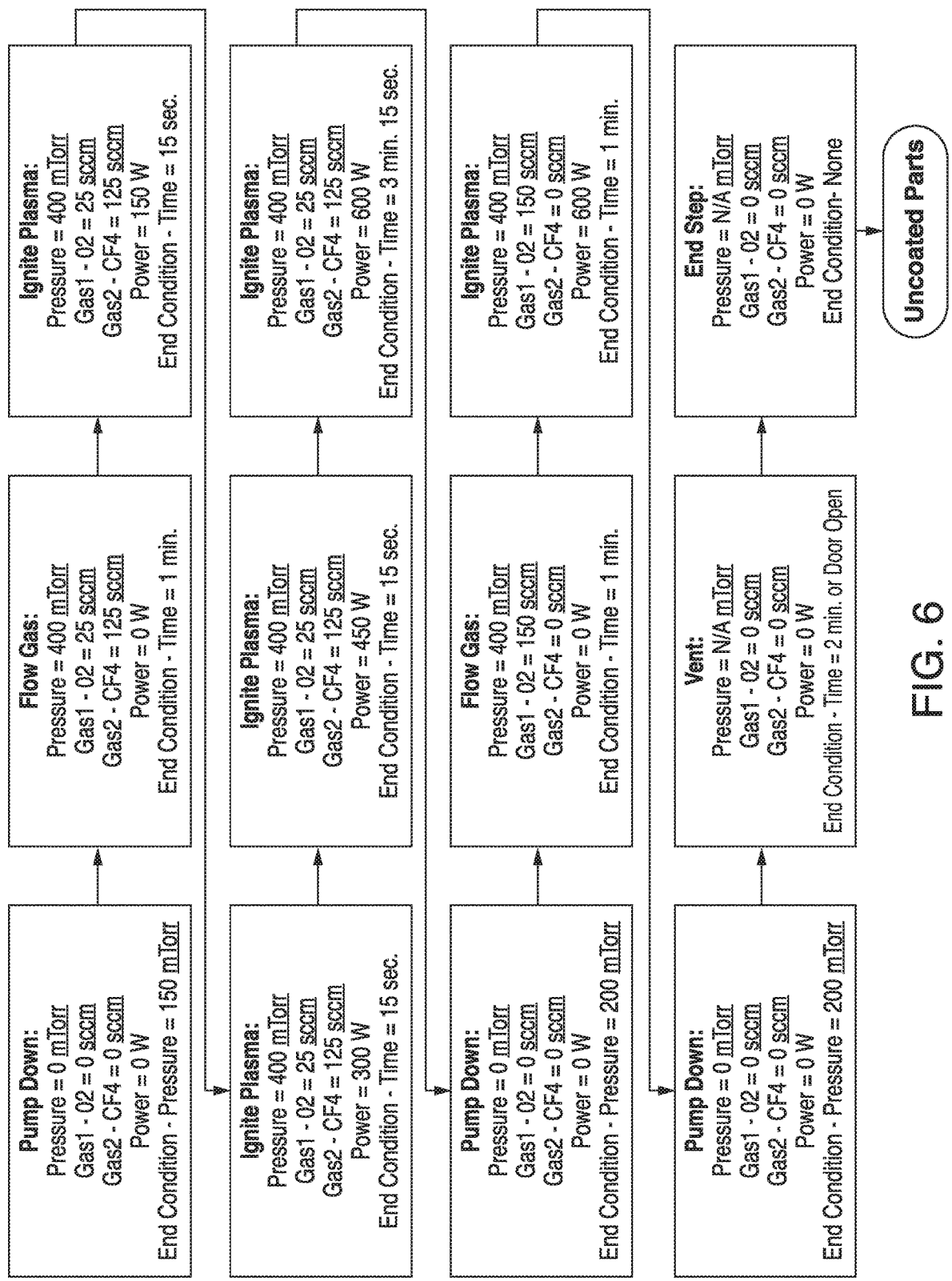
FIG. 6 is a flow chart of a method for removing the non-stick coating from the jaw members according to an aspect of the present disclosure.

With reference to FIG. 6, a process for removing the non-stick coating 400 is described. This process may be implemented at a reprocessing facility that reconditions previously-used medical devices. After the forceps 10 have been used and the jaw members 110 and 120 are covered in eschar and other tissue byproducts due to electrosurgical treatment, the process of FIG. 6 may be used to remove the non-stick coating 400 and apply a new coating as described above with respect to FIG. 5.

Reprocessing may involve disassembling wholly or partially the forceps 10, and in particular, detaching the jaw members 110 and 120 from the shaft 12. The forceps 10 may also be sterilized. Sterilization of the forceps 10 may occur prior to or following disassembly. Once the jaw members 110 and 120 are detached, the jaw members 110 and 120 are placed into the chamber of the plasma system to remove the non-stick coating 400. In some embodiments, the removal process, as described below in FIG. 6, may also be utilized to sterilize the jaw members 110 and 120.

With reference to FIG. 6, after used jaw members are loaded into the chamber, the chamber is pumped down until vacuum is established. Into the vacuumed chamber, oxygen and tetrafluoromethane are supplied at their respective flow rates until a set point pressure is reached. Oxygen flow rate may be from about 10 SCCM to about 50 SCCM, in embodiments may be about 25 SCCM. Tetrafluoromethane flow rate may be from about 75 SCCM to about 200 SCCM, in embodiments may be about 125 SCCM. Set point pressure may be from about 100 mTorr to about 700 mTorr, in embodiments, set point pressure may be about 400 mTorr. Once the desired pressure is reached, plasma is ignited for a plurality of periods (e.g., first, second, third, fourth, etc. periods) at progressively increasing power levels. The first three periods maybe about the same amount of time with the last period being the longest and applying power at the highest level. The first time period may be about 15 seconds and the first power level may be 150 watts. The second time period may be about 15 seconds and the second power level may be 300 watts. The third time period may be about 15 seconds and the third power level may be 450 watts. The fourth time period may be about 3.25 minutes and the fourth power level may be 600 watts. Following this process, the non-stick coating 400 is removed.

Once the non-stick coating 400 is removed, the chamber is pumped down. After the vacuum is established, oxygen is supplied into the chamber at any suitable rate until a set point pressure is reached. Gas flow rate may be from about 50 SCCM to about 400 SCCM, in embodiments, the flow rate may be about 150 SCCM. Set point pressure may be from 200 mTorr to about 6,000 mTorr, in embodiments the pressure may be 400 mTorr. Once the desired pressure is reached, oxygen plasma is ignited for a fifth period of time at a fifth power level to finalize the second layer. The fifth time period may be about 1 minute and the fifth power level may be 600 watts. The chamber is then pumped down again and vented. Following application of oxygen plasma, the jaw members 110 and 120 are cleaned and the non-stick coating 400 may be reapplied by the reprocessor as described above with respect to FIG. 5. In particular, the jaw members 110 and 120 once coated, may then be reassembled with previously-sterilized components of the forceps 10.

Figure 7:
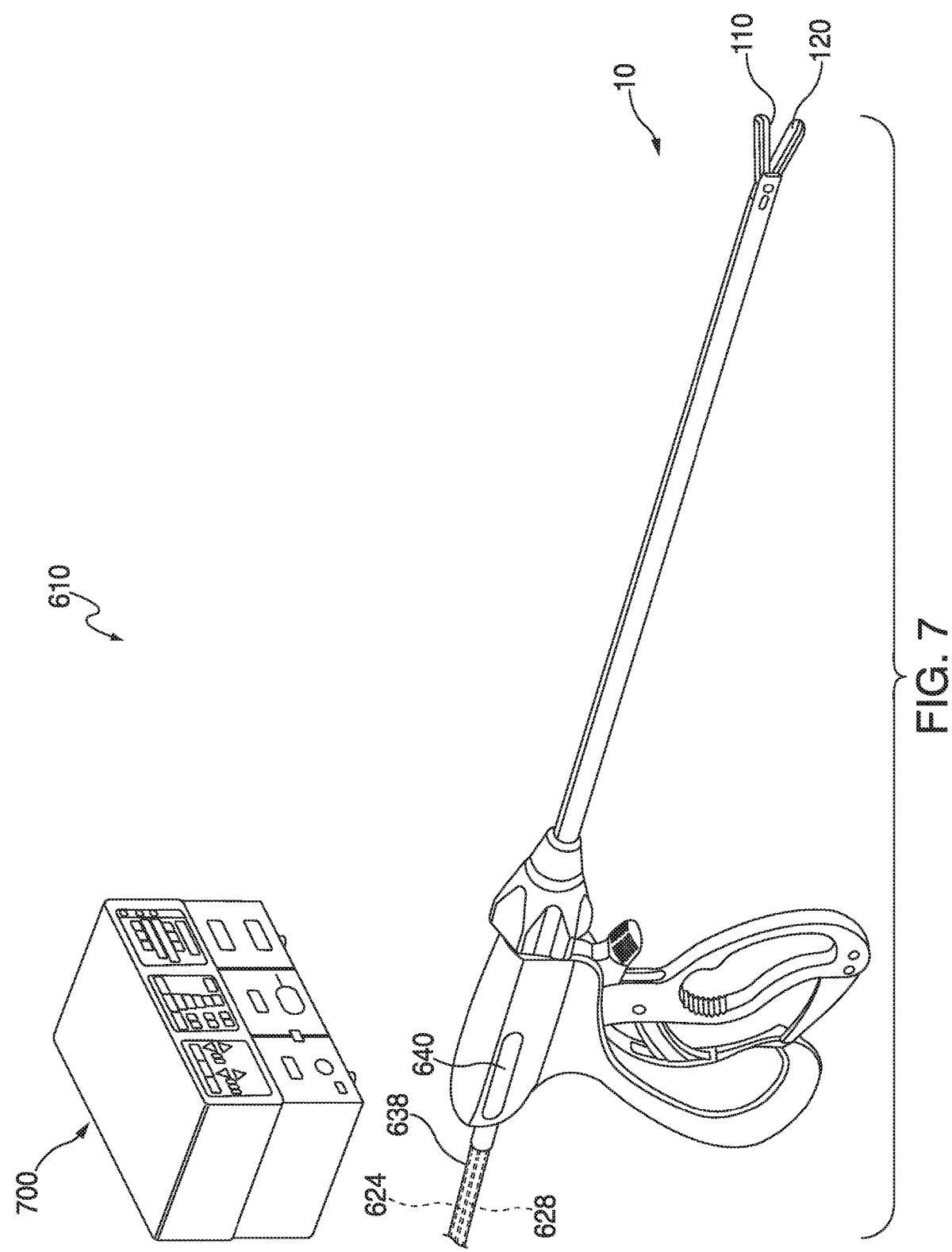
FIG. 7 is a perspective view of an electrosurgical system according to an aspect of the present disclosure.

FIG. 7 is a perspective view of the components of one illustrative embodiment of an electrosurgical system 610 according to the present disclosure. The system 610 may include an electrosurgical generator 700 configured to couple to the forceps 10 (FIG. 1), forceps 100 (FIG. 2), or any other suitable electrosurgical instrument. One of the jaw members 110 or 120 of the forceps 10 acts as an active electrode with the other jaw member being a return electrode. Electrosurgical alternating RF current is supplied to the active electrode of the forceps 10 by a generator 700 via a supply line 624 that is connected to an active terminal 730 (FIG. 7) of the generator 700. The alternating RF current is returned to the generator 700 from the return electrode via a return line 628 at a return terminal 632 (FIG. 7) of the generator 700. The supply line 624 and the return line 628 may be enclosed in a cable 638

The forceps 10 may be coupled to the generator 700 at a port having connections to the active and return terminals 730 and 732 (e.g., pins) via a plug (not shown) disposed at the end of the cable 638, wherein the plug includes contacts from the supply and return lines 624, 628 as described in more detail below.

Figure 8:
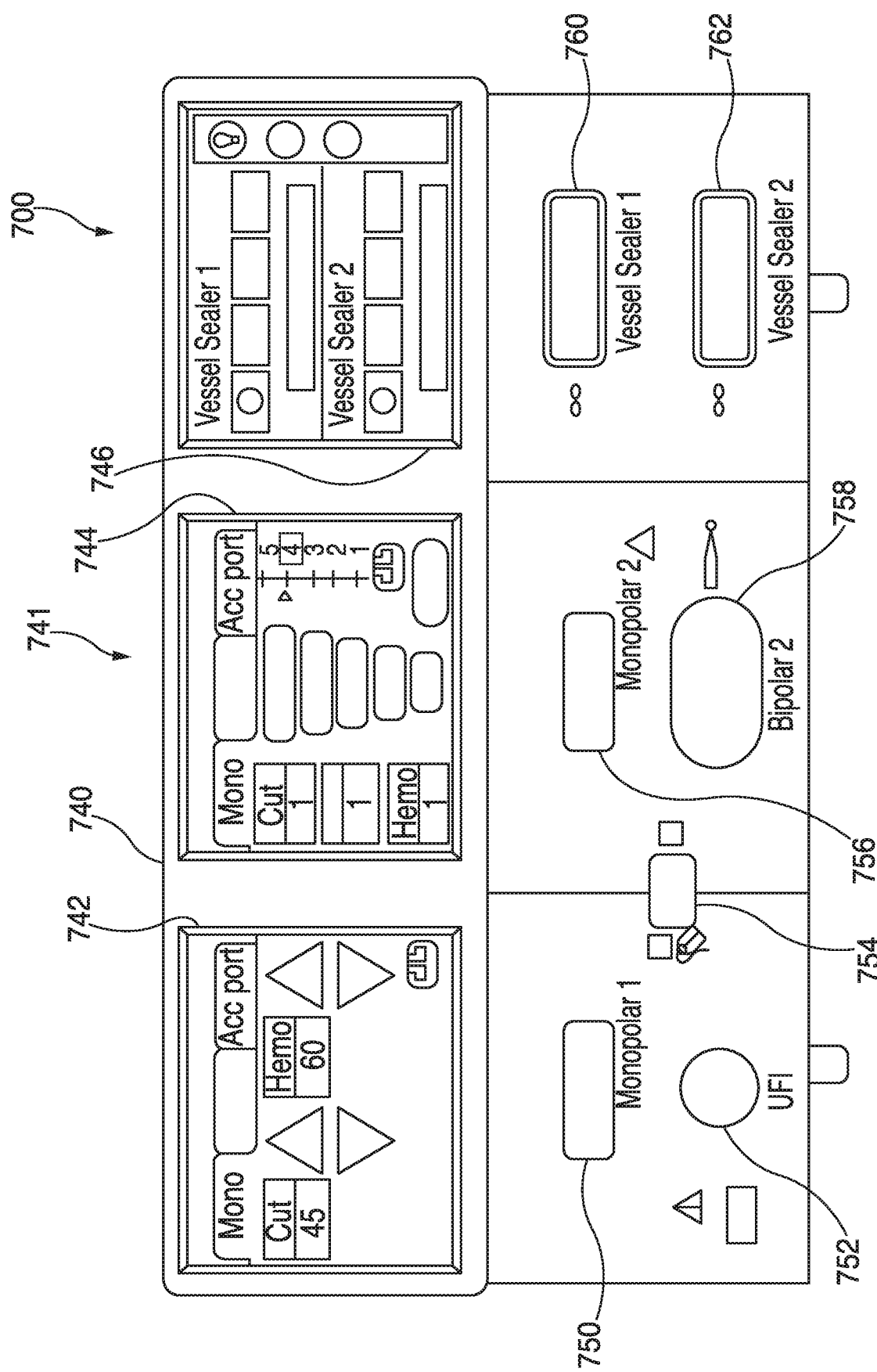
FIG. 8 is a front view of an electrosurgical generator of the electrosurgical system of FIG. 7 according to an aspect of the present disclosure.

With reference to FIG. 8, a front face 740 of the generator 700 is shown. The generator 700 may include a plurality of ports 750-762 to accommodate various types of electrosurgical instruments (e.g., monopolar electrosurgical instrument, forceps 10, forceps 100, etc.).

The generator 700 includes a user interface 741 having one or more display screens 742, 744, 746 for providing the user with variety of output information (e.g., intensity settings, treatment complete indicators, etc.). Each of the screens 742, 744, 746 is associated with a corresponding port 750-762. The generator 700 includes suitable input controls (e.g., buttons, activators, switches, touch screen, etc.) for controlling the generator 700. The screens 742, 744, 746 are also configured as touch screens that display a corresponding menu for the instruments (e.g., forceps 10). The user then adjusts inputs by simply touching corresponding menu options.

Screen 642 controls monopolar output and the devices connected to the ports 750 and 752. Port 750 is configured to couple to a monopolar electrosurgical instrument and port 752 is configured to couple to a foot switch (not shown). The foot switch may be used to provide for additional inputs (e.g., replicating inputs of the generator 700). Screen 744 controls monopolar and bipolar output and the devices connected to the ports 756 and 758. Port 756 is configured to couple to other monopolar instruments. Port 758 is configured to couple to a bipolar instrument (not shown).

Screen 746 controls the forceps 10 that may be plugged into one of the ports 760 and 762, respectively. The generator 700 outputs energy through the ports 760 and 762 suitable for sealing tissue grasped by the forceps 10. In particular, screen 746 outputs a user interface that allows the user to input a user-defined intensity setting for each of the ports 760 and 762. The user-defined setting may be any setting that allows the user to adjust one or more energy delivery parameters, such as power, current, voltage, energy, etc. or sealing parameters, such as energy rate limiters, sealing duration, etc. The user-defined setting is transmitted to a controller 724 (FIG. 9) where the setting may be saved in memory. In embodiments, the intensity setting may be a number scale, such as for example, from one to ten or one to five. In embodiments, the intensity setting may be associated with an output curve of the generator 700. The intensity settings may be specific for each forceps 10 being utilized, such that various instruments provide the user with a specific intensity scale corresponding to the forceps 10. The active and return terminals 730 and 732 (FIG. 9) may be coupled to any of the desired ports 750-762.

With continued reference to FIG. 8, each of the ports 750-762 may include a reader, such as an optical reader or a radio frequency interrogator, configured to communicate with the forceps 10 to extract data pertaining to the forceps 10. Such data may be encoded in a barcode, an RFID tag, computer-readable storage, or any other data storage medium 640, which may be disposed on the forceps 10 or any of its components, such as the cable 638. In embodiments, the data may include whether the forceps 10 includes coated or uncoated jaw members 110 and 120. In further embodiments, the data may also include properties of the coating, such as its thickness, dielectric properties, current and voltage limits, temperature limits, and the like.

Figure 9:
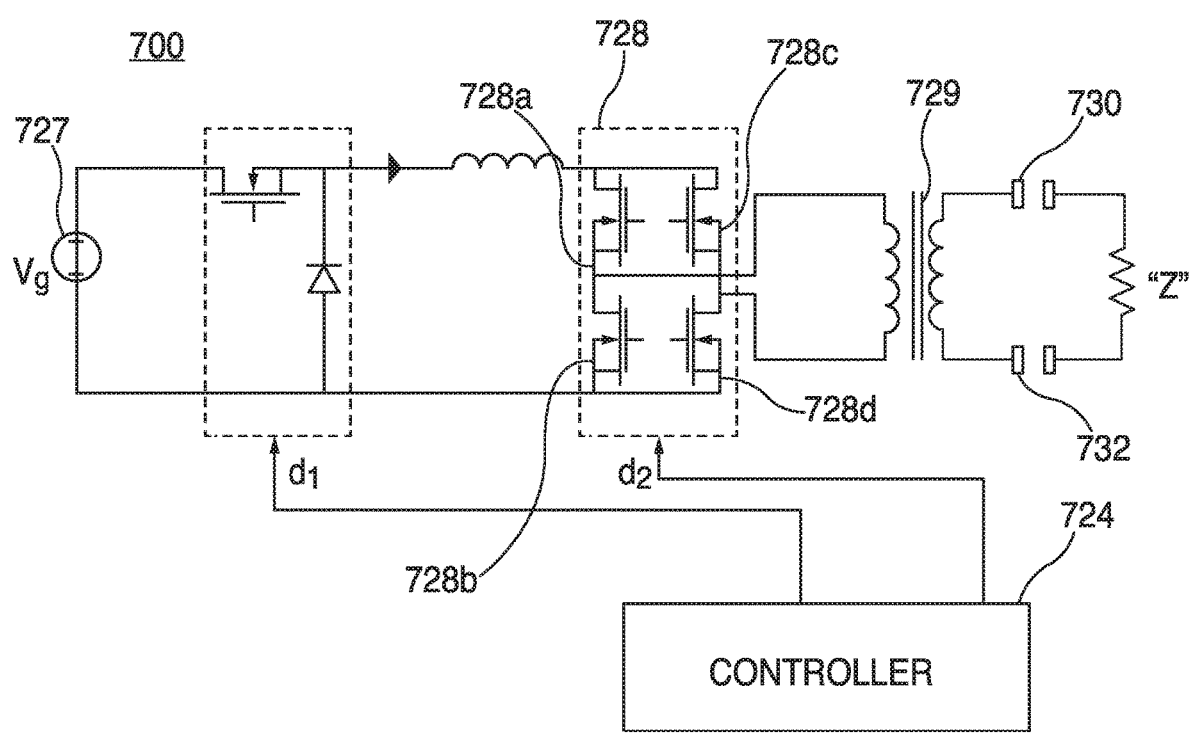
FIG. 9 is a schematic diagram of the electrosurgical generator according to an aspect of the present disclosure.

FIG. 9 shows a schematic block diagram of the generator 700, which includes a controller 724, a power supply 727, and a power converter 728. The power supply 727 may be a high voltage, DC power supply connected to an AC source (e.g., line voltage) and provides high voltage, DC power to the power converter 728, which then converts high voltage, DC power into RF energy and delivers the energy to the active terminal 730. The energy is returned thereto via the return terminal 732. The active and return terminals 730 and 732 are coupled to the power converter 728 through an isolation transformer 729.

The power converter 728 is configured to operate in a plurality of modes, during which the generator 700 outputs corresponding waveforms having specific duty cycles, peak voltages, crest factors, etc. It is envisioned that in other embodiments, the generator 700 may be based on other types of suitable power supply topologies. Power converter 728 may be a resonant RF amplifier or a non-resonant RF amplifier, as shown. A non-resonant RF amplifier, as used herein, denotes an amplifier lacking any tuning components, i.e., inductors, capacitors, etc., disposed between the power converter and a load "Z," e.g., tissue coupled through forceps 10.

The controller 724 includes a processor (not shown) operably connected to a memory (not shown), which may include one or more of volatile, non-volatile, magnetic, optical, or electrical media, such as read-only memory (ROM), random access memory (RAM), electrically-erasable programmable ROM (EEPROM), non-volatile RAM (NVRAM), or flash memory. The processor may be any suitable processor (e.g., control circuit) adapted to perform the operations, calculations, and/or set of instructions described in the present disclosure including, but not limited to, a hardware processor, a field programmable gate array (FPGA), a digital signal processor (DSP), a central processing unit (CPU), a microprocessor, and combinations thereof. Those skilled in the art will appreciate that the processor may be substituted for by any logic control circuit adapted to perform the calculations and/or execute a set of instructions described herein.

The controller 724 includes an output port that is operably connected to the power supply 727 and/or power converter 728 allowing the processor to control the output of the generator 700 according to either open and/or closed control loop schemes. A closed loop control scheme is a feedback control loop, in which a plurality of sensors measure a variety of tissue and energy properties (e.g., tissue impedance, tissue temperature, output power, current and/or voltage, etc.), and provide feedback to the controller 724. The controller 724 then controls the power supply 727 and/or power converter 728, which adjusts the DC and/or power supply, respectively.

The generator 700 according to the present disclosure may also include a plurality of sensors (not shown). The sensors may be coupled to the power supply 727 and/or power converter 728 and may be configured to sense properties of DC current supplied to the power converter 728 and/or RF energy outputted by the power converter 728, respectively. The controller 724 also receives input signals from the input controls of the generator 700 and/or forceps 10. The controller 724 utilizes the input signals to adjust power outputted by the generator 700 and/or performs other control functions thereon.

Power converter 728 includes a plurality of switching elements 728a-728d arranged in an H-bridge topology. In embodiments, power converter 728 may be configured according to any suitable topology including, but not limited to, half-bridge, full-bridge, push-pull, and the like. Suitable switching elements include voltage-controlled devices such as transistors, field-effect transistors (FETs), combinations thereof, and the like. In embodiments, the FETs may be formed from gallium nitride, aluminum nitride, boron nitride, silicon carbide, or any other suitable wide bandgap materials. In further embodiments, the FETs may be any suitable FETs, such as conventional silicon FETs.

The controller 724 is in communication with both power supply 727 and power converter 728. Controller 724 is configured to output control signals, which may be a pulse-width modulated ("PWM") signal, to switching elements 728a-728d as described in further detail in co-pending application published as U.S. Patent Application Publication No. 2014/0254221, the entire contents of which are incorporated by reference herein. In particular, controller 724 is configured to modulate a control signal $d_1$ supplied to power supply 727 and control signal $d_2$ supplied to switching elements 728a-728d of power converter 728. Additionally, controller 724 is configured to calculate power characteristics of generator 700, and control generator 700 based at least in part on the measured power characteristics.

The controller 724 is configured to execute a vessel sealing algorithm which controls the output of the generator 700 to treat tissue (e.g., seal vessels). Exemplary algorithms are disclosed in commonly-owned U.S. Pat. No. 8,147,485 and U.S. Patent Application Publication No. 2016/0045248, the entire disclosures of all of which are incorporated by reference herein.

Algorithms according to the present disclosure may be embodied as software instructions executable by controller 724. In embodiments, an algorithm may be an impedance-based energy delivery algorithm in which energy is delivered by the generator 700 to the tissue until a predetermined impedance threshold is met or otherwise controlled based on measured tissue impedance. In view of the non-stick coating 400, the storage medium 640 of the forceps 10 may include data pertaining to the non-stick coating 400 as described above. During use, the controller 724 may extract the data regarding the non-stick coating 400 from the storage medium and adjust the vessel sealing algorithm based on one or more coating properties extracted from the storage medium 640. More specifically, the controller 724 may be configured to adjust one or more parameters of the vessel sealing algorithm based on the coating properties extracted from the storage medium 640. In embodiments, the algorithm may include a completion threshold (e.g., impedance, phase difference, etc.) that is used by the controller 724 to determine whether a vessel seal is complete. The controller 724 may be configured to adjust the completion threshold based on the data pertaining to the non-stick coating 400. In embodiments, the controller 724 may be configured to adjust other parameters of the energy delivery algorithm based on coating data stored in the storage medium 640. This allows the generator 700 to tailor energy application based on whether the jaw members 110 and 120 of the forceps 10 are coated or uncoated, since the non-stick coating 400 may affect dielectric and electric properties of the forceps 10.

All numerical values and ranges disclosed above may vary by some amount. Whenever a numerical range with a lower limit and an upper limit is disclosed, any number and any included range falling within the range are specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Unless the meaning is clearly to the contrary, all ranges set forth herein are deemed to be inclusive of the endpoints. Unless specifically stated or obvious from context, as used herein, the term "about" when used in conjunction with a stated numerical value or range denotes somewhat more or somewhat less than the stated value or range, to within a range of ±10% of that stated value or range.

EXAMPLES

Example 1

This Example compares non-coated jaw members with jaw members having a non-stick coating formed from plasma polymerization of HMDSO according to the present disclosure.

Four sets of jaw members of LIGASURE™ LF4318 IMPACT™ instruments available from Medtronic of Minneapolis, Minn. were used in this Example. Three of the jaw members were coated with three different thicknesses of 50 nm, 100 nm, and 150 nm. The fourth jaw members were left uncoated.

During testing, the jaw members were connected to a VALLEYLAB™ FORCETRIAD™ electrosurgical generator available from Medtronic of Minneapolis, Minn. The generator was used to energize the jaw members to seal tissue for testing. A force measurement station was also setup, which included an electrical motor coupled to a drive rod for opening and closing the jaw members. The jaw members were also encased in dielectric tissue clamps surrounding the jaw members, which allowed for additional clamping about the tissue. The drive rod was connected to a bi-directional load cell, which was connected to LABVIEW® from National Instruments of Austin, Tex. for recording load cell measurements. LABVIEW® was also used to control the motor to open and close the jaw members.

Porcine uterine mesometrium was used as test tissue. During testing, the jaw members were closed by the motor and the generator was activated to seal the tissue. After the seal was completed, the clamp was held in place, while the jaw members were opened. The load cell measured the force during the opening of the jaw members and LABVIEW® recorded the maximum observed force as the sticking force. Each of the four jaw members was tested about one hundred times. A blank opening force (e.g., without sealed tissue) was measured approximately every twenty seals to account for variable opening force of different jaw members. This blank force value was used as a calibration value and subtracted from the recorded sticking force for each subsequent seal.

Figure 10:
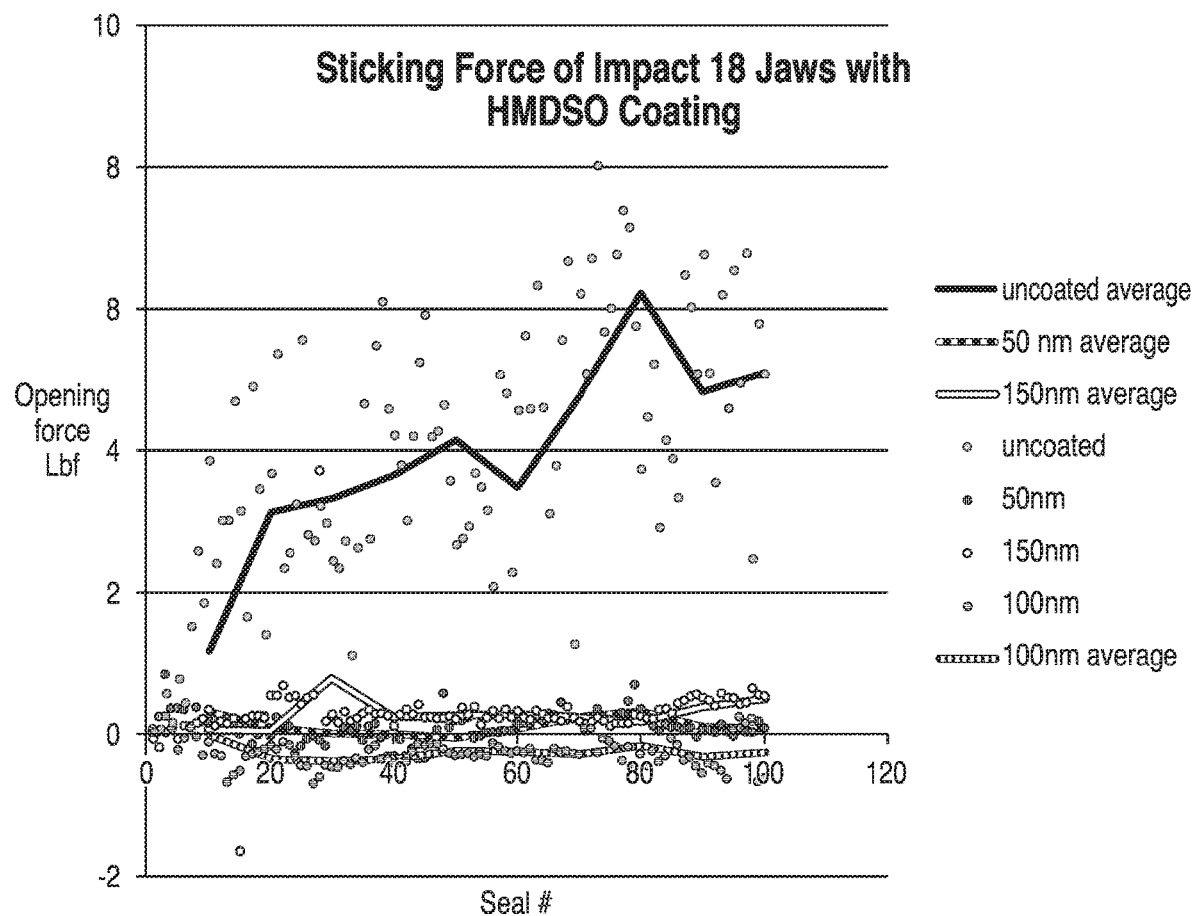
FIG. 10 is a plot of sticking force plots of uncoated and coated jaw members according to an aspect of the present disclosure.

With reference to FIG. 10, which shows sticking force plots for each of the for jaw members, all three coated devices displayed about 0 lbf sticking force over the course of the test. There was not a measureable difference between sticking forces of the three coated jaw members. The uncoated device however displayed about 1 lbf sticking force at the start of the testing sequence and increasing up to 6 lbf by the end of the 100 seals.

Although there was no measureable difference between the average sticking force of three coated jaw members, there was a visual difference in the jaws after the sealing was complete. The uncoated control jaw members had a large amount of eschar build up on the housing portion of the jaw as well as some on the seal plates themselves. The 50 nm coated jaw members had some blood and one spot of eschar build up on the plastic. The 100 nm coated jaw members had very little blood and eschar build up, and the 150 nm coated jaw members had almost no build-up or eschar of any kind. This shows that while there was no difference in sticking force for the coated jaw members, there was an observable reduction in build-up (e.g., eschar) for higher thicknesses of coating. Thus, the non-stick coating according to the present disclosure was effective in preventing tissue sticking when compared to uncoated jaw members.

Example 2

This Example compares jaw members having a non-stick coating formed from plasma polymerization of HMDSO according to the present disclosure with jaw members of other vessel sealers.

For this Example, six jaw members of LIGASURE™ IMPACT™ instruments were used along with jaw members of ENSEAL™ G2 Super Jaw instrument available from Ethicon Inc. of Somerville, N.J. and THUNDERBEAT™ Open Extended Jaw instrument available from Olympus of Center Valley, Pa. Three of the LIGASURE™ IMPACT™ jaw members were coated using the non-stick coating according to the present disclosure and the remaining three instruments were uncoated. Each of the ENSEAL™ and THUNDERBEAT™ were not modified in any way.

Each of the instruments was paired to a specific electrosurgical generator. VALLEYLAB™ FT10, FORCETRIAD™, and LS10 available from Medtronic were connected to one of coated and uncoated jaw members of IMPACT™ instruments, such that each of the coated and uncoated IMPACT™ instruments was paired with a different generator. In addition, the ENSEAL™ instrument was coupled to Ethicon's G11 generator and the THUNDERBEAT™ instrument was coupled to Olympus' ESG-400 (electrosurgical) and USG-400 (ultrasonic) generators since the THUNDERBEAT™ instrument is a dual-modality instrument.

The same force measurement station and tissue testing process was used to measure sticking force of each of the instrument/generator combinations, for a total of ten combinations. Each of the combinations was used to perform one hundred and ten (110) sealing cycles, ten (10) seals in eleven (11) rounds. Approximately 15-35 minute breaks were taken between each round. Sticking force was measured and recorded for each of the sealing cycles.

The sticking evaluation involved a qualitative assessment made at the time of the seal, by the laboratory technician. In general, if the tissue did not fall away from the jaw members, the jaw members would be opened and closed several times to attempt to detach tissue. After two or three opening/closing sequences, tissue would be removed by graspers or by hand. If the tissue removed from the jaw members it was considered to be non-sticking, and if the tissue stretched as it was being pulled away from the jaw members it was considered to be sticking.

With respect to the THUNDERBEAT™ instrument, since it is an ultrasonic device where the tissue between the jaw members is cut as part of the seal cycle, sticking evaluation involved determining whether the tissue stuck to a portion of the top jaw (e.g., non-active jaw). For the ENSEAL™ instrument there were many different types of sticking. The most common was when the jaw members were stuck and did not spring back open after actuation. This required manual intervention to either pull the jaw members apart or force the jaw handle to open. There were also many times when jaws opened, but the tissue was stuck to a portion of the bottom jaw members. For the IMPACT™ instruments on all three generators, the sticking was observed to be in the form of tissue being adhered to a portion of the jaw members and not falling away readily. There were no instances of the jaw members not opening on these instruments.

A summary of the sticking results for are shown in Table 1 below. Table 1 includes the number of seals with sticking under the "yes" column and without sticking the "no" column, as well a percentage of seals that were classified as sticking. In Table 1, LF4418 refers to the coated IMPACT™ instrument, whereas LF4318 refers to the uncoated IMPACT™ instrument with a suffix representing the generator being used (FT for FORCETRIAD™, FT10, or LS10).

TABLE 1

Summary of Sticking Results

| Device Type | Device ID | Sticking Count Yes | Sticking Count No | % of Seals With Sticking |
|---|---|---|---|---|
| LF4418 | 4418FT | 45 | 65 | 41% |
|  | 4418FT10 | 18 | 92 | 16% |
|  | 4418LS10 | 12 | 98 | 11% |
| LF4318 | 4318FT | 77 | 33 | 70% |
|  | 4318FT10 | 83 | 27 | 75% |
|  | 4318LS10 | 91 | 19 | 83% |
| ThunderBeat | TB | 29 | 81 | 26% |
| G2 Super Jaw | SJ | 88 | 22 | 80% |

The results of the statistical analysis are summarized in Table 2 below, with the P value for each comparison of interest in addition to a description of the outcome. The coated IMPACT™ instrument tested on the FORCETRIAD™ generator and the THUNDERBEAT™ instrument had statistically less sticking (P=0.032) and the ENSEAL™ and uncoated IMPACT™ instrument tested on the FORCETRIAD™ both had statistically more sticking (P<0.001 for both). The coated IMPACT™ instrument tested on the FT10 generator there was no statistical difference in the rate of sticking compared to the THUNDERBEAT™ instrument (P=0.099). The ENSEAL™ instrument and the uncoated IMPACT™ instrument tested on the FT10 generator both had statistically more sticking (P<0.001). The IMPACT™ instrument tested on the LS10 generator, the THUNDERBEAT™ instrument (P=0.005), ENSEAL™ instrument (P<0.001), and uncoated IMPACT™ instrument tested on the LS10 generator (P<0.001) all had statistically more sticking.

TABLE 2

Summary of Exact Test Results

| Control Device ID | Test Device ID | Exact Test | Result |
|---|---|---|---|
| LF4418FT | TB | P = 0.032 | TB statistically less sticking |
|  | SJ | P < 0.001 | SJ statistically more sticking |
|  | LF4318FT | P < 0.001 | LF4318FT statistically more sticking |
| LF4418FT10 | TB | P = 0.099 | No statistical difference |
|  | SJ | P < 0.001 | SJ statistically more sticking |
|  | LF4318FT10 | P < 0.001 | LF4318FT10 statistically more sticking |
| LF4418LS10 | TB | P = 0.005 | TB statistically more sticking |
|  | SJ | P < 0.001 | SJ statistically more sticking |
|  | LF4318LS10 | P < 0.001 | LF4318LS10 statistically more sticking |

A rate of sticking on the coated IMPACT™ instrument was compared to the uncoated IMPACT™ instrument, the ENSEAL™ instrument, and the TUNDERBEAT™ instrument. The ENSEAL™ instrument had statistically more sticking when compared to the coated IMPACT™ instrument on any of the VALLEYLAB™ generators. Comparing the coated IMPACT™ instrument with the uncoated IMPACT™ instrument (on their respective generator combinations) the coated IMPACT™ instrument had statistically less sticking overall. When compared to the FORCETRIAD™ and coated IMPACT™ instrument combination, the THUNDERBEAT™ had statistically less sticking. However, when compared to the FT10 generator there was no statistical difference in sticking, and when compared to the LS10 generator, the THUNDERBEAT™ device had statistically more sticking. Thus, the non-stick coating according to the present disclosure was effective in preventing tissue sticking when compared to uncoated jaw members and other coated instruments. In addition, effectiveness of the non-stick coating was also dependent on the type of generator being used. Thus, the generator's power supply and/or its control algorithm were also a factor.

What is claimed is:

1. A method of inhibiting tissue from sticking to an electrically conductive component of an electrosurgical tissue sealing device during application of energy to tissue, the method comprising:
    applying a non-stick coating on at least a portion of the electrically conductive component of the electrosurgical tissue sealing device using a plasma enhanced chemical vapor deposition technique; and
    controlling a thickness of the non-stick coating to be from about 35 nm to about 85 nm, wherein the non-stick coating is applied to inhibit tissue from sticking to the electrically conductive component during application of energy to the tissue and to permit a sensing of at least one tissue parameter generated via application of energy to the tissue.

2. The method according to claim 1, wherein the non-stick coating includes polydimethylsiloxane.

3. A method of inhibiting tissue from sticking to an electrically conductive component of an electrosurgical tissue sealing device during application of energy to tissue, the method comprising:
    applying a non-stick coating on at least a portion of the electrically conductive component of the electrosurgical tissue sealing device using a plasma enhanced chemical vapor deposition technique; and
    controlling a thickness of the non-stick coating to be about 60 nm, wherein the non-stick coating is applied to inhibit tissue from sticking to the electrically conductive component during application of energy to the tissue and to permit a sensing of at least one tissue parameter generated via application of energy to the tissue.

4. An electrosurgical system comprising:
    an electrosurgical energy source;
    an electrosurgical instrument configured to couple to the electrosurgical energy source, the electrosurgical instrument including:
        a pair of opposing jaw members configured to grasp tissue;
        a pair of electrically conductive tissue sealing plates coupled respectively to the pair of opposing jaw members, the pair of electrically conductive tissue sealing plates configured to deliver electrosurgical energy to tissue, the electrosurgical energy source configured to sense at least one tissue parameter generated by delivery of electrosurgical energy to the tissue via the pair of electrically conductive tissue sealing plates; and
        a non-stick coating including polydimethylsiloxane having a thickness of from about 35 nm to 85 nm disposed on at least a portion of each of the pair of electrically conductive tissue sealing plates and having a thickness controlled to:
            reduce sticking of the tissue to each of the electrically conductive tissue sealing plates; and
            permit sensing of the at least one tissue parameter.

5. The electrosurgical system according to claim 4, wherein the non-stick coating has a thickness of about 60 nm.

6. The electrosurgical system according to claim 4, wherein the at least one tissue parameter is selected from the group consisting of temperature and impedance.

* * * * *